(12) United States Patent
Hung et al.

(10) Patent No.: US 11,506,664 B1
(45) Date of Patent: Nov. 22, 2022

(54) METHODS FOR DETECTING AND TREATING CHOLANGIOCARCINOMA

(71) Applicants: Academia Sinica, Taipei (TW); National Tsing Hua University, Hsinchu (TW)

(72) Inventors: Shang-Cheng Hung, Taipei (TW); Gwo-Bin Lee, Hsinchu (TW); Priya Gopinathan, Hsinchu (TW)

(73) Assignees: Academia Sinica, Taipei (TW); National Tsing Hua University, Hsinchu (TW)

( * ) Notice: Subject to any disclaimer, the term of this patent is extended or adjusted under 35 U.S.C. 154(b) by 69 days.

(21) Appl. No.: 17/238,431

(22) Filed: Apr. 23, 2021

(51) Int. Cl.
*G01N 33/574* (2006.01)
*C08B 37/00* (2006.01)
(Continued)

(52) U.S. Cl.
CPC ..... *G01N 33/57438* (2013.01); *A61K 31/505* (2013.01); *A61K 31/53* (2013.01);
(Continued)

(58) Field of Classification Search
CPC ............ G01N 33/57438; A61K 33/243; A61K 31/505; A61K 31/53; A61K 31/7068; A61K 31/7072; C08B 37/0006
See application file for complete search history.

(56) References Cited

FOREIGN PATENT DOCUMENTS

WO    WO-03016915 A1 * 2/2003 ......... A61K 38/1709

OTHER PUBLICATIONS

Gopinathan et al., "Exploring Circulating Tumor Cells in Cholangiocarcinoma Using a Novel Glycosaminoglycan Probe on a Microfluidic Platform", Apr. 24, 2020, Advanced Healthcare Materials.

* cited by examiner

*Primary Examiner* — Michael P Cohen

(57) ABSTRACT

Disclosed herein is a novel compound of formula (I) for detecting circulating cancerous cells, particularly, cholangio-cancerous cells, from a biological sample,

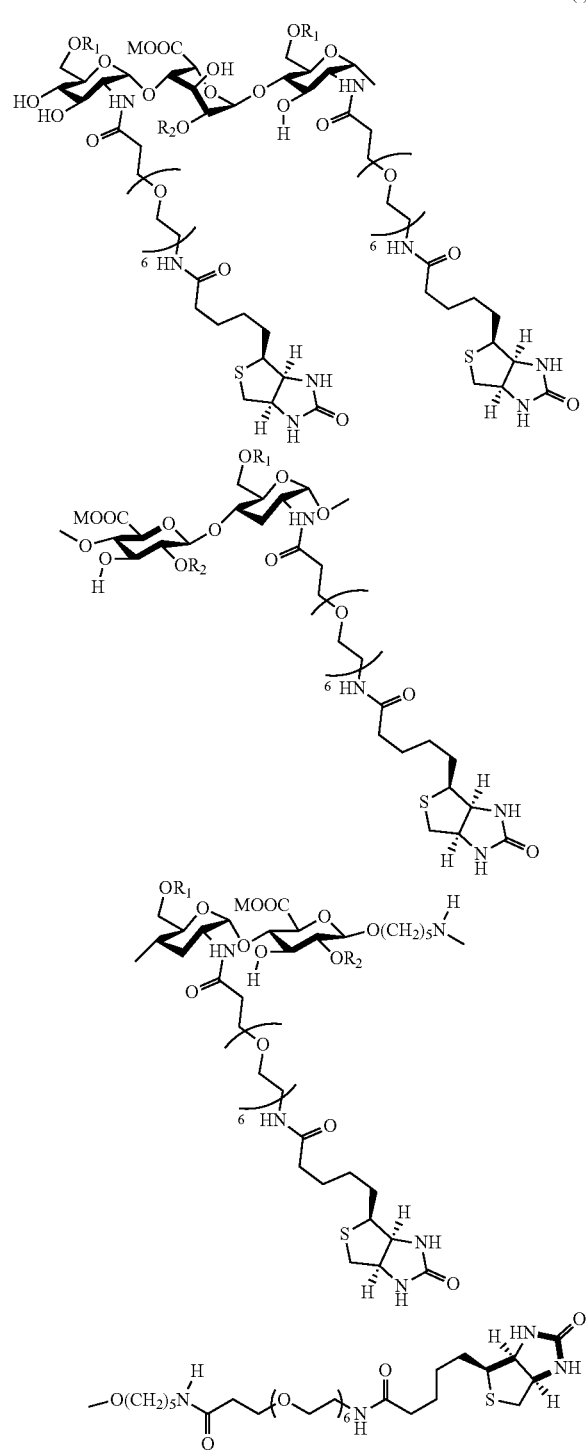

(I)

wherein, $R_1$ and $R_2$ are independently H, or —$SO_3M$; and M is a monovalent cation selected from the group consisting of sodium ion, potassium ion, lithium ion or ammonium ion. Also disclosed herein is a method of treating and detecting cholangio-cancerous cells from a biological sample of a (Continued)

subject suspected of having cholangiocarcinoma (CCA). The method includes steps of, contacting the biological sample with a magnetic bead pre-coated with the compound of formula (I); detecting a complex formed between the magnetic bead and the biological sample in an immunoassay; and administering to the subject an effective amount of a chemotherapeutic agent to ameliorate symptoms associated with the CCA.

12 Claims, 4 Drawing Sheets

(51) Int. Cl.
*A61K 33/243* (2019.01)
*A61K 31/53* (2006.01)
*A61K 31/7072* (2006.01)
*A61K 31/505* (2006.01)
*A61K 31/7068* (2006.01)

(52) U.S. Cl.
CPC ...... *A61K 31/7068* (2013.01); *A61K 31/7072* (2013.01); *A61K 33/243* (2019.01); *C08B 37/0006* (2013.01)

METHODS FOR DETECTING AND TREATING CHOLANGIOCARCINOMA

STATEMENT REGARDING PRIOR DISCLOSURES BY THE INVENTOR OR A JOINT INVENTOR UNDER 37 C.F.R. 1.77(B)(6)

Part of the subject matter of the invention described in the present application was published by the inventors, Shang-Cheng Hung, Gwo-Bin Lee, and Priya Gopinathan in an article titled "Exploring Circulating Tumor Cells in Cholangiocarcinoma Using a Novel Glycosaminoglycan Probe on a Microfluidic Platform." The article was published in Advanced Healthcare Materials 2020, 9: 1901875. The publication was made by and/or originated from 3 members of the inventive entity of the present invention, and the entirety of this article is incorporated herein by reference. A copy of the article is provided in a concurrently filed Information Disclosure Statement pursuant to the guidance of 78 Fed. Reg. 11076 (Feb. 14, 2013)."

BACKGROUND OF THE INVENTION

1. Field of the Invention

The present disclosure in general relates to compounds and methods for the detection of circulating cancerous cells in a biological sample.

2. Description of Related Art

Cholangiocarcinoma (CCA) is the second most common primary malignant liver cancer occurring at the bile ducts which drain bile juice from the liver into the small intestine. It is typically characterized by late-stage diagnosis, poor prognosis, high recurrence and frequent metastasis. Nowadays, imaging techniques, including ultrasonography, magnetic resonance imaging and computed tomography, and pathological diagnoses by forceps biopsy or brush cytology are the main tools applied to detect CCA. These methods are limited by tumor sizes, localization and lesions so that they are unable to discover CCA tumor at the early stage. The most common tumor biomarkers used to diagnose CCA are carbohydrate antigen 19-9 (CA19-9) and carcinoembryonic antigen (CEA). However, the sensitivity and specificity of CA19-9 and CEA are still not satisfactory in clinical applications.

Circulating tumor cells (CTCs) have been suggested to play a role in the metastatic spread of carcinomas, accordingly, they may serve as markers for the detection of tumors, particularly, those that metastasized. However, their application in the clinical assessment of CCA remains inclusive. Quantification of a relatively low number of CTCs against a background of millions of blood cells has thwarted progress in CCA diagnosis, and affinity-based isolation techniques using CTC-specific antigens such as EpCAM, EphB4, HER2, EGFR, CEA and etc failed to produce results suffice for clinical applications.

Therefore, three exists in the related art a need of new biomarkers for detection CTCs in a biological sample, which in turn may provide prognosis on CCA.

SUMMARY OF THE INVENTION

Inventors of the present invention unexpectedly identify novel octasaccharides that bind to the surface of cholangio-cancerous cells, thus these octasaccharides are useful for detecting cholangio-cancerous cells in a biological sample of a subject, whom is at risk of developing cholangiocarcinoma (CCA) or has CCA.

Accordingly, the first aspect of the present disclosure is directed to a compound of formula (I),

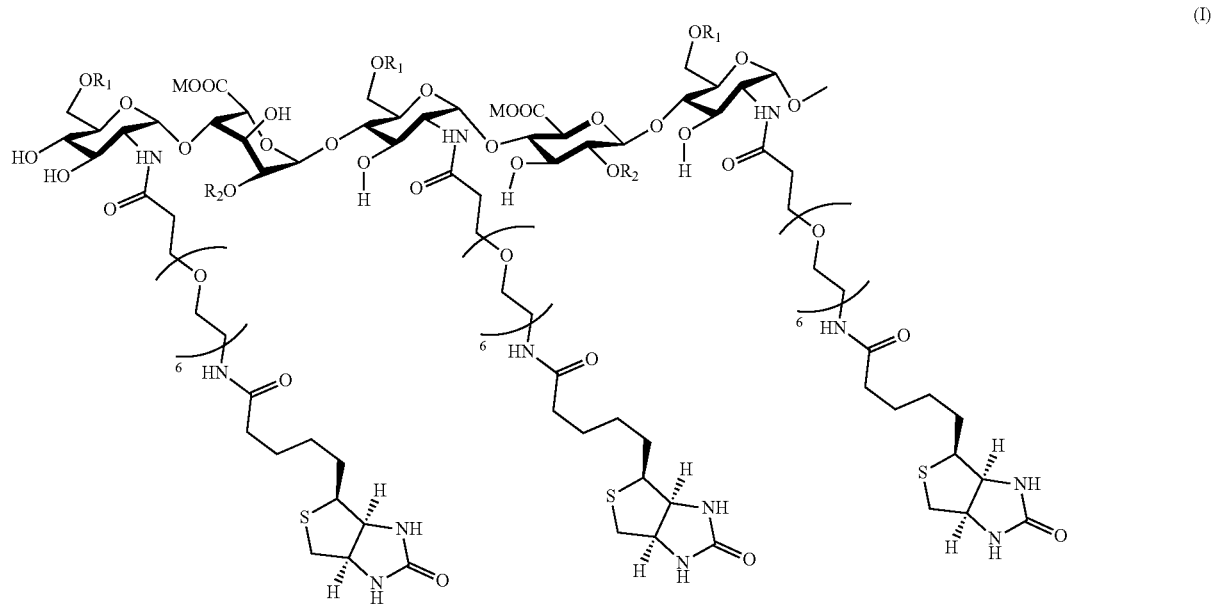

-continued

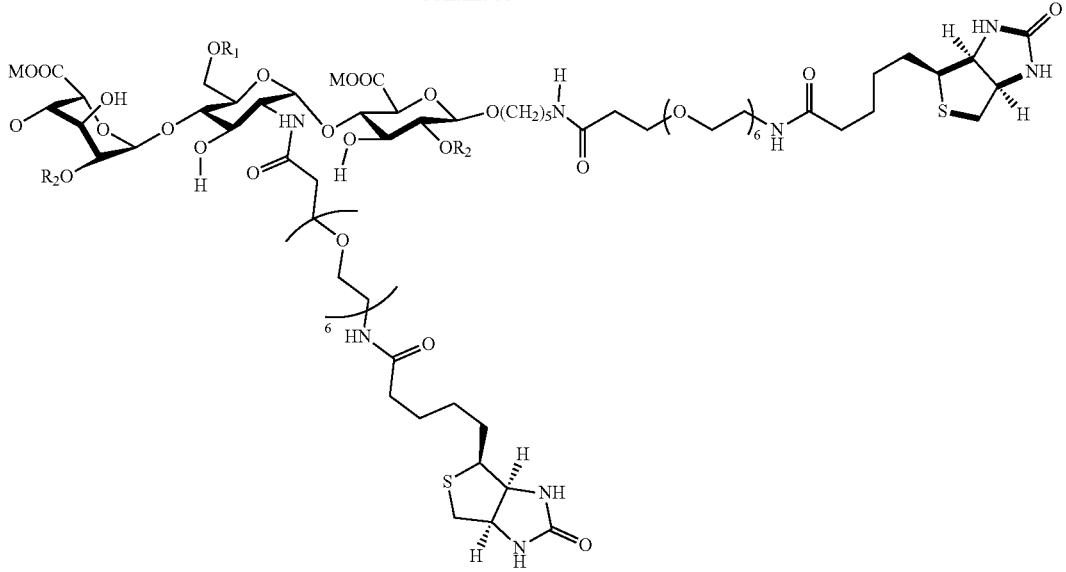

Wherein $R_1$ and $R_2$ are independently H, or —$SO_3M$; and M is a monovalent cation selected from the group consisting of sodium ion, potassium ion, lithium ion or ammonium ion.

According to one preferred embodiment of the present disclosure, in the formula (I), $R_1$ and $R_2$ are independently —$SO_3M$, and M is the sodium ion.

The second aspect of the present disclosure is directed to a method of treating and detecting circulating cholangiocancerous cells from a biological sample of a subject suspected of having CCA. The method includes the steps of, (a) contacting the biological sample with a compound of formula (I); and (b) detecting a complex formed between the compound of formula (I) and the biological sample in an immunoassay; and (c) administering to the subject an effective amount of a chemotherapeutic agent to ameliorate symptoms associated with the CCA.

According to preferred embodiments of the present disclosure, the compound of formula (I) is coupled to streptavidin, which is conjugated to the outer surface of a magnetic bead.

According to preferred embodiments of the present disclosure, in the compound of formula (I), $R_1$ and $R_2$ are independently —$SO_3M$, and M is the sodium ion.

Examples of the biological sample suitable for use in the present method include, but are not limited to, blood, plasma, serum, urine, sputum, saliva, tissue sample, biopsy, and tissue lysate. Preferably, the biological sample is the blood from the subject.

According to preferred embodiments of the present disclosure, the subject has stage III or IV CCA, or metastatic CCA.

According to optional embodiment of the present disclosure, the method further comprises, before the step (a), pre-treating the blood with a lysis buffer, so as to lyse red blood cells therein.

Examples of the chemotherapeutic agent suitable for use in the present method include, but are not limited to, S-1, leucovorin, oxaliplatin, gemcitabine, cisplatin, and a combination thereof. In some embodiments, the method comprises administering to the subject an effective amount of the S-1 to ameliorate symptoms associated with the CCA, in which the S-1 is a combination of tegafur, 5-chloro-2,4-dihydropyrimidine (CDHP), and potassium oxonate. In other embodiments, the method comprises administering to the subject an effective amount of a combination of gemcitabine and cisplatin to ameliorate symptoms associated with the CCA. In still further embodiments, the method comprises administering to the subject an effective amount of a combination of S-1, leucovorin, oxaliplatin, and gemcitabine to ameliorate symptoms associated with the CCA.

According to optional embodiment of the present disclosure, the method further comprises administering to the subject a radiotherapy in addition to the administration of S-1 to ameliorate symptoms associated with the CCA.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF THE PREFERRED EMBODIMENTS

Figure 1A:
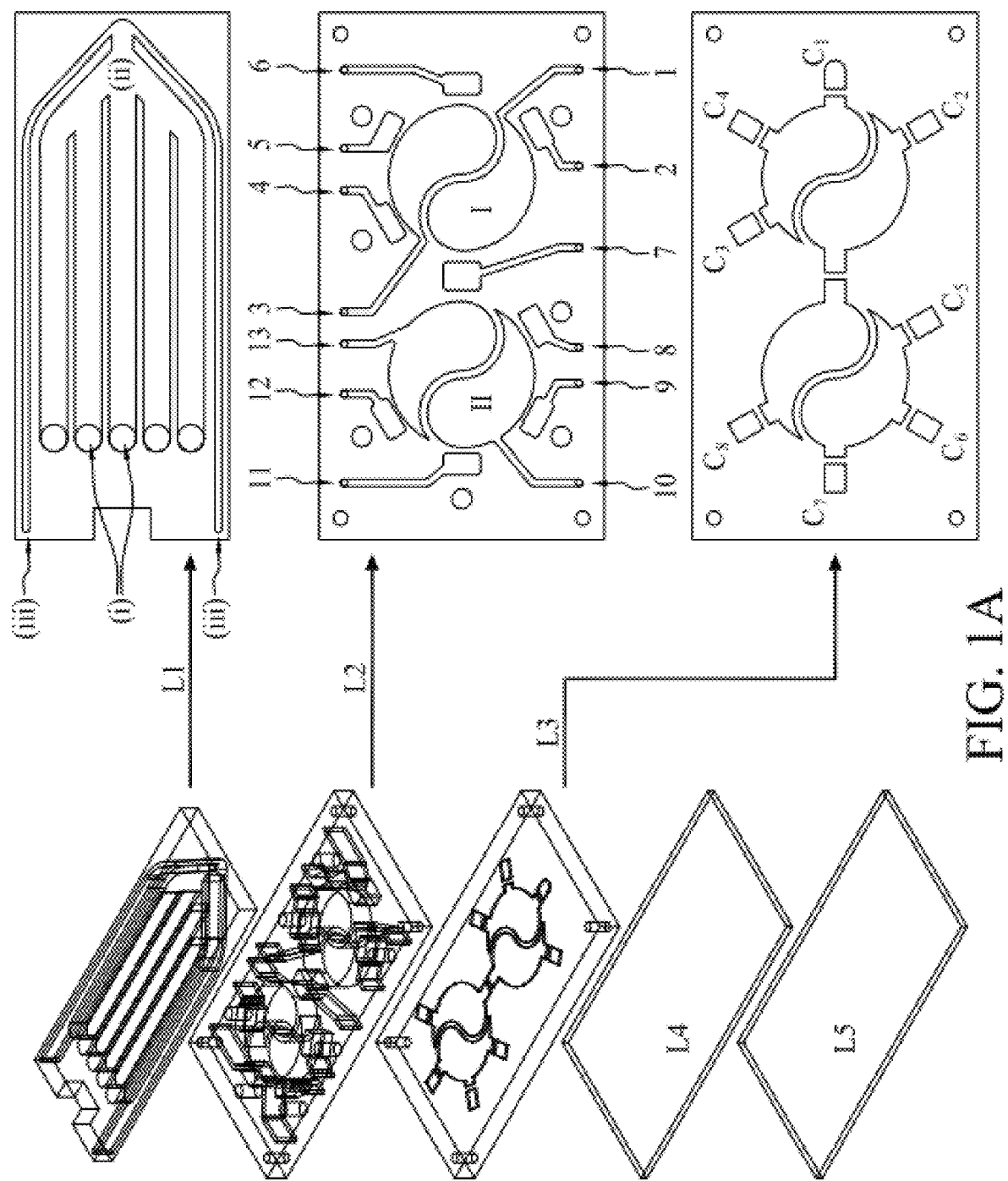
FIG. 1A: Schematic diagrams of a microfluidic chip. The chip features all layers from L1 to L5 representing liquid channel layer, air control layer, liquid channel layer, thin PDMS layer and double-sided tape, respectively. Detail structure of layers L1, L2 and L3 are shown where (i) represents inlets for lysed blood, (ii) represents pellet collection area, and (iii) represents outlets for waste collection. (I) represents the blood treatment unit, and (II) represents the immunofluorescence staining unit. The 13 connections to electromagnetic valves (EMVs) for pneumatic control of the chip are shown as 1 to 13. The 8 microchambers/reagent storing units are labeled as $C_1$ to $C_8$. $C_1$: cell pellet collection unit, $C_2$: waste collection unit, $C_3$: magnetic bead storage unit, $C_4$ and $C_5$: 1× phosphate-buffered saline (PBS) storage unit, $C_6$: the storage unit for secondary antibody (i.e., DyLight 488 and CD45-PE first and later for DAPI), $C_7$: waste collection unit, and $C_8$: anti-CK17 primary antibody storage unit.

The detailed description provided below in connection with the appended drawings is intended as a description of the present disclosure and is not intended to represent the only forms in which the present disclosure may be constructed or utilized.

1. Definitions

Unless otherwise indicated, the term "patient" or "subject" may be used interchangeably in the present disclosure, and refers to any animal. The animal can be a human subject, or a non-human subject. The subject may be a human, but can also be a mammal in need of veterinary treatment, e.g., domestic animals or game animals, farm animals, and laboratory animals (e.g., rats, mice, guinea pigs, primates, and the like). Usually the animal is a non-human mammal, such as a non-human primate. Non-human primates include chimpanzees, cynomologous monkeys, spider monkeys, and macaques, e.g., Rhesus or Pan. Domestic animals and game animals include cows, horses, pigs, sheep, deer, bison, buffalo, mink, felines (e.g., domestic cats, canines (e.g., dogs)), wolf and fox, avian species (e.g., chicken, turkey, and ostrich), and fish (e.g., trout, catfish, and salmon).

The term "contacting" is used herein with respect to a cell (e.g., a cell in a biological sample) and refers to any mode of delivery or "administration" of an agent either to cells or the biological sample, in which the agent (e.g., a compound of the present disclosure or a magnet bead pre-coated with the compound of the present disclosure) is brought into contact with one or more cells in sufficient amount to achieve affinity binding therebetween.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. The Compound of the Present Invention

Aspects of the present disclosure relate to the finding that a novel octasaccharide is useful as a biomarker for the identification and/or detection of cancerous cells in a biological sample. The novel octasaccharide is described herein.

In one aspect, the present invention relates to a compound of formula (I):

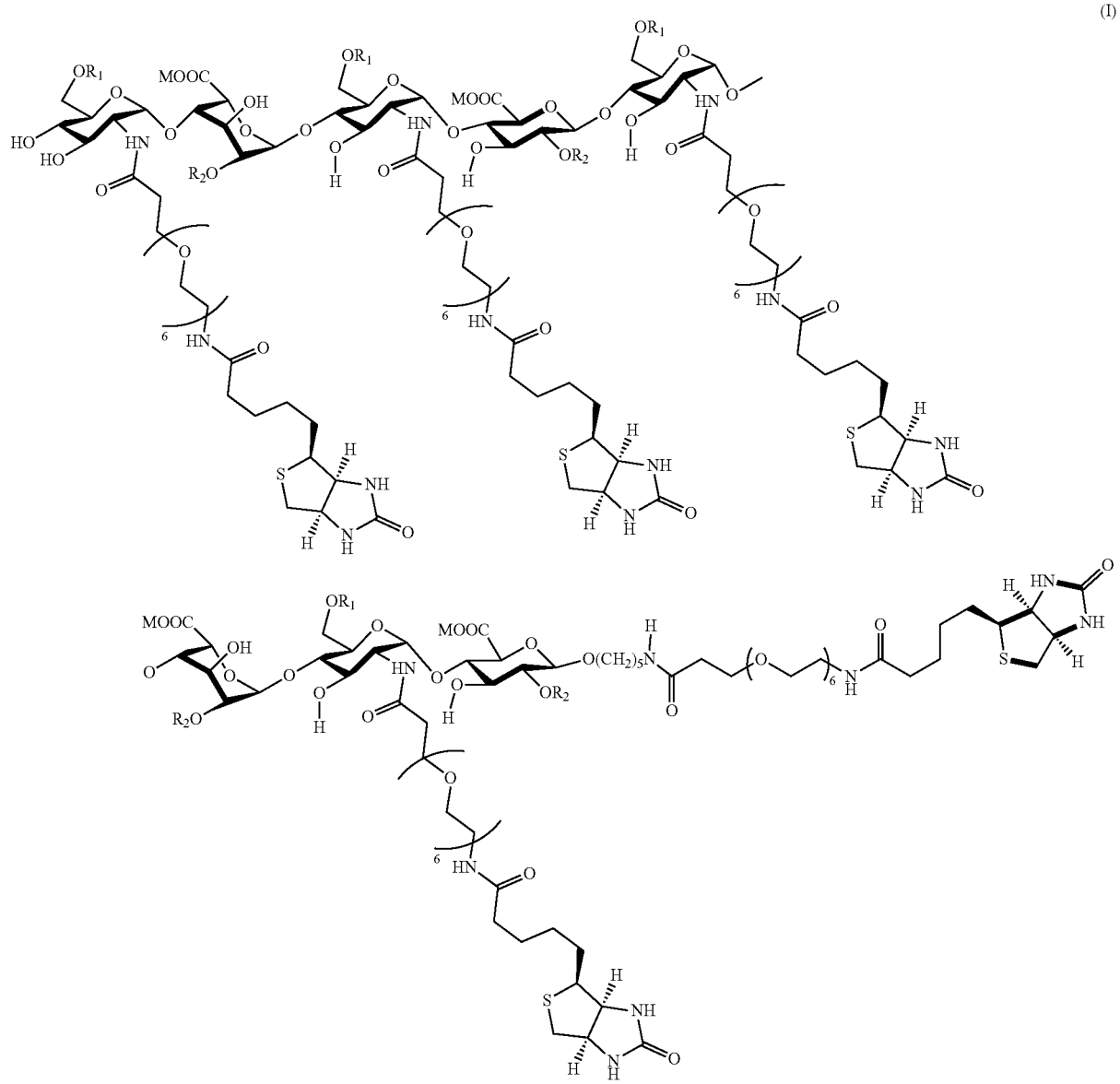

Wherein, $R_1$ and $R_2$ are independently H, or —$SO_3M$; and M is a monovalent cation selected from the group consisting of sodium ion, potassium ion, lithium ion or ammonium ion.

In some embodiments of the present disclosure, in the formula (I), $R_1$ and $R_2$ are independently —$SO_3M$, and M is the sodium ion.

The compound of the present disclosure may be prepared in accordance with procedures described in the working examples. All stereoisomers of the present compounds, such as those which may exist due to asymmetric carbons on the R substituents of the compound of formula (I) including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

3. Method of Use

The compound of formula (I) may bind to surfaces of cancerous cells, particularly cancers originated from cholangio bile duct. Accordingly, the present disclosure thus encompasses a method of identifying or detecting cholangio-cancerous cells from a biological sample of a subject suspected of having cholangiocarcinoma (CCA), as well as a method of treating the subject based on the detection of cholangio-cancerous cells in the biological sample.

The present method includes contacting a biological sample of the subject with a compound of formula (I), in which a binding between the compound of formula (I) and the biological sample indicates the presence of cholangio-cancerous cells in the biological sample. Alternatively, or optionally, for better identification or detection of cholangio-cancerous cells in the blood sample, the blood sample is pre-treated with a lysis buffer, which will result in the lysis of red blood cells in the blood sample, prior to commencing the present method (i.e., prior to contacting the blood with magnetic beads). Examples of the biological sample suitable for use in the present method, include but are not limited to, blood, plasma, serum, urine, sputum, saliva, tissue sample, biopsy, and tissue lysate. In one preferred embodiment, the biological sample is blood. Accordingly, the method comprises mixing a blood sample of the subject with the present compound. Upon mixing, if the blood sample does contain cholangio-cancer cells, they will automatically bind with the compound of formula (I) and form a complex, which may be detected via any suitable means, such as enzyme-linked immunosorbent assay (ELISA), immunofluorescent staining and the like; and the presence of the complex is an indication that the subject is positive for CCA. By contrast, if the blood sample does not contain cholangio-cancer cells, there will not be a binding between the blood sample and the compound of formula (I), and the absence of the binding is an indication that the subject is negative for CCA. Preferably, the compound of formula (I) is coated on the surface of a magnetic bead via coupling to streptavidin pre-conjugated on the outer surface of the magnetic bead. Thus, upon mixing with the biological sample, the magnetic beads having the compound of formula (I) coated thereon would be able to capture the cholangio-cancerous cells present in the biological sample, and the magnetic beads having cholangio-cancerous cells captured thereon may be allocated and harvested via use of a magnet.

Upon confirming the subject's disease status, particularly, when the subject is positive for CCA, suitable treatment (e.g., radiotherapy, chemotherapy and the like) may then be administered to the subject to ameliorate symptoms associated with the CCA. In some embodiments, the method therefore includes administering an effective amount of a chemotherapeutic agent to the subject. Examples of the chemotherapeutic agent suitable for use in the present method include, but are not limited to, S-1, leucovorin, oxaliplatin, gemcitabine, cisplatin, and a combination thereof. In some embodiments, an effective amount of the S-1 is administered to the subject to ameliorate symptoms associated with the CCA, in which the S-1 is a combination of tegafur, 5-chloro-2,4-dihydropyrimidine (CDHP), and potassium oxonate. In optional embodiments, a radiotherapy is administered to the subject before, concurrently with, or after the administration of the S-1. In other embodiments, a combination of gemcitabine and cisplatin is administered to the subject to ameliorate symptoms associated with the CCA. In further embodiments, a combination of S-1, leucovorin, oxaliplatin, and gemcitabine is administered to the subject to ameliorate symptoms associated with the CCA.

According to preferred embodiments of the present disclosure, the subject has stage III or IV CCA, or metastatic CCA.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Conjugation of the Present Compound to Magnetic Beads

Compound 20 ($100 \times 10^{-6}$ M) was incubated with Dynabeads MyOne streptavidin C1 ($\approx 7\text{-}10 \times 10^9$ beads mL$^{-1}$, Ø=1 µm, Invitrogen, USA) magnetic beads in a volume/volume ratio of 1:10 and placed on an RM-2L INTELLI-mixer (ELMI Ltd., Latvia) at 25 rpm for 30 min at room temperature (C2 mode). The beads were then collected using a magnetic particle concentrator (MPC, Dynabeads MPC-1, Life Technologies) for 2 min. The supernatant was discarded, and the beads were washed thrice with 1 mL of deionized water (DI water). The bead conjugates MB-SCH45 were suspended in the same volume of DI water as the initial volume of Dynabeads used.

Blood Specimen Collection

Informed written consent was obtained from all 65 advanced stage or metastatic CCA patients. The three healthy blood samples used in this study were collected from Tainan blood bank, Taiwan. For each donor, peripheral blood (10 mL) was drawn into BD Vacutainer spray coated K2EDTA tubes (BD Diagnostics, USA). All samples were maintained and transported at 4° C. and processed within 30 h of collection. To avoid bias, samples were blindly processed without prior information on the disease status, cancer stage, or metastasis in patients.

Experimental Set-Up

The experimental procedure involved four steps: (1) RBC lysis and isolation of pellet, (2) negative depletion for the removal of WBCs, (3) positive magnetic enrichment, and 4) immunofluorescence staining.

(1) RBC Lysis and Isolation of Pellet

RBC were lysed by adding 9 mL of 1×RBC lysis buffer (Biolegend, USA) to 1 mL of peripheral blood and incubating at room temperature with gentle mixing on a rotary shaker (TKS ROCKER-S-01, Lab666, Taiwan) for 5 min. Then the sample was dispensed into the topmost PDMS layer of the chip through the inlets provided (FIG. 1A). The microfluidic chip was then spun as described above and placed on a PMMA plate with a groove such that the microfluidic chip could be placed inside it. It was then placed on a spin-coater (M and R Nanotechnology Co. Taoyuan, Taiwan) and spun at 1,200 rpm for 2 min at a negative gauge pressure of −67 kPa and the cell pellet was then moved into the blood treatment unit of the chip's liquid channel layer by a vacuum force created by the microvalves. The waste blood with lysed RBCs was removed through the waste outlets (marked as (iii) in FIG. 1A) using vacuum suction. The remaining 5 mL of lysed blood was then dispensed into the topmost layer of the microfluidic chip and the above process was repeated. The pellet was transported to the micromixer and suspended in 180 µL of 1× phosphate buffered saline (PBS) by activating the micromixer for 2 min. The resulting cell suspension consisting of predominately nucleated cells was then subjected to negative depletion for the removal of leucocytes.

(2) Negative Depletion and Positive Magnetic Enrichment

A negative depletion strategy reliant on the removal of leucocytes via their binding to anti-CD45 Ab bound to magnetic beads (Dynabeads CD45, Thermo-Fisher Scientific) was employed herein on-chip. The cell-bead complexes were then attracted to a magnet to remove the bound leukocytes from the lysed blood samples. After four rounds of negative depletion, the remaining cells (predominantly CTCs) in the collected supernatant were mixed with MB-SCH45 (bead conjugated with compound 20 described above) or MB-anti-EpCAM (EpiEnrich, $4 \times 10^8$ beads mL$^{-1}$, Ø=4.5 µm, Thermo-Fisher Scientific). The magnetic bead-CTC complexes were then collected, washed, and transferred to the immunofluorescence staining unit of the chip for further analysis.

(3) Immunofluorescence Staining

For immunofluorescence staining, primary anti-CK17 (1:500 dilution; 100 µL, 0.6 mg mL$^{-1}$, GTX103765, Rabbit, GeneTex, USA) was used. The secondary Ab, goat antirabbit IgG DyLight 488; GeneTex and anti-CD45-PE (RRID: AB_10375163, HUCD45 PE, Life Technologies) were used at a dilution of 1:500. It is to be noted here that the anti-CD45 Ab used had a PE tag thereby requiring no primary Ab. DAPI (1 mg mL$^{-1}$, Thermo Fischer, US) was then used as the nuclear stain. After the final magnetic collection, the bead-cell complexes were suspended in 10 µL of 1×PBS and collected through the waste collection chamber. They were transferred onto the numbered microscopic slide and ProLong Gold Antifade Reagent (Invitrogen) was used to embed the cell-bead complexes.

The numbered microscope slide was fabricated using an SU-8 standard photolithography process to facilitate CTC counting. Concisely, a 30 µm thick layer of SU-8 3035 (MicroChem, USA) was spin-coated on a glass microscope slide. A soft-baking process for 10 min was performed and the SU-8 microstructures were patterned at a dosage of 147 mJ/cm$^2$ of ultraviolet light exposure. A post-exposure bake at 65° C. for 1 min and 95° C. for 5 min was performed followed by a standard SU-8 developing process. The glass slide featuring the microstructures was formed and then analyzed under the microscope using a DS-Qi1Mc camera equipped with a Peltier cooling device and a programmable gain amplifier (Nikon) coupled to an inverted microscope equipped with a digital control module. The software used was NIS-Elements Basic Research software (Br, version 4.20.00, 64 bit, Nikon). A cell was considered to be CTC if it (1) expressed CK (an internal architectural protein that is largely associated with epithelial cells), (2) was characterized by a high nuclear: cytoplasmic ratio (upon DAPI staining), and (3) did not express CD45.

Assessment of CTCs in Metastatic CCA Patients Before and After Chemotherapy

The role of CTCs was investigated in response to treatment effectiveness assessment by analyzing blood samples (1 mL) before and after chemotherapy in five patients with advanced or metastatic CCA for a period of six months. The presence and number of CTCs in blood were assessed using the prior mentioned MB-SCH45 alongside MB-anti-EpCAM followed by immunofluorescence staining along with the conventional FACS and tumor size measurements were performed using CT scan. For CT scan measurements, the solid tumors were measured in at least one dimension with the longest diameter as per RECIST guideline. Before initiating chemotherapy, baseline studies of CTC enumeration from blood and radiographic analysis were performed within an average of 3 days prior to starting treatment. Blood samples from five CCA patients were obtained at 4-12-week intervals and the same type of imaging studies were performed with an average of 4 days between imaging and the blood draw.

Construction of a Microfluidic Chip

Figure 1B:
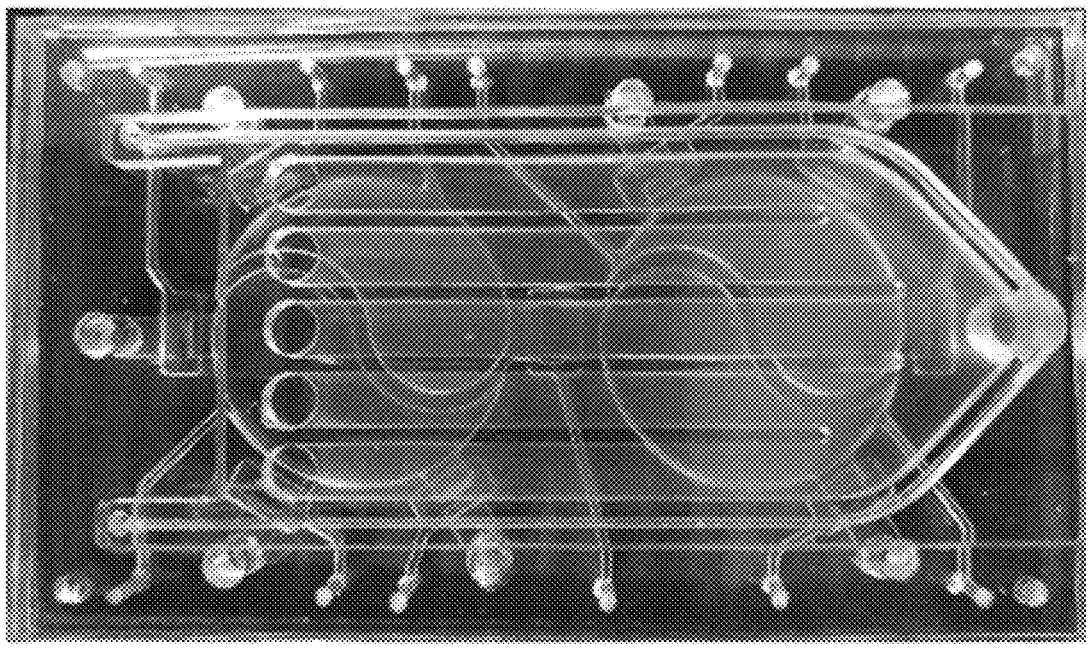
FIG. 1B: Photograph of the microfluidic chip of FIG. 1A.

In order to efficiently capture cancerous cells by using magnetic beads, an integrated microfluidic chip was constructed and used in the present study. The microfluidic chip was composed of 4 polydimethylsiloxane (PDMS) layers and a double-sided tape layer (FIG. 1). The uppermost PDMS of the chip was used for collection of cell pellet from blood, and the second and third layers were the air control and the liquid layer, respectively. The fourth (bottom) layer of the chip was the thinnest and provided enough support to keep the contents of the liquid channel intact. All layers were bonded together via oxygen plasma treatment (FC-12064, FEMTO Science, USA) at 90 W for 1 min, which also introduced polar functional silanol (SiOH) groups, changing the surface properties of PDMS from being hydrophobic to hydrophilic. The chip was then treated with a solution of Pluronic P123 (a triblock copolymer of poly(ethylene oxide)-poly(propylene oxide)-poly(ethylene oxide)) in 99% (by weight) aqueous ethanol to increase hydrophilicity of PDMS. P123 was dispensed into the topmost layer of the chip and allowed to react with PDMS for 5 min. Microvalves were actuated so that P123 solution was transported to the chip's liquid layer and finally through the waste collection chambers. The chip was capable of performing various fluidic functions (e.g., mixing, transportation and etc.) using two types of air, compressed air and suction pressure (i.e., vacuum). The flow of compressed air or generation of suction pressure was controlled by electromagnetic valves (EMVs). The entire set up for operation of the chip was consisted of an air compressor, a vacuum pump, and a computer controlled EMV functional unit.

The microfluidic chip as depicted in FIG. 1A featured two closed type micromixer/micropump/transportation units. As shown in FIG. 1A, blood after lysis was dispensed into the topmost PDMS layer through the inlet (i) of the chip. The channel labelled (iii) served as vent for any bubbles trapped during dispensing lysed blood into the inlets, it also served as waste collection unit for the lysed blood after collection of the pellet. The chamber $C_1$ was designed such as to ensure no pellet loss after collection and direct transfer of the afore-said to the micromixer I of the liquid channel layer (L2). The second and third PDMS layer (L2 and L3) were used for positive enrichment and immunostaining procedures operated pneumatically via active mechanical displacement of two microvalves and an actuation chamber. The air control layer of the chip was divided into two parts: the first and second micromixers. The first micromixer (I in FIG. 1A) served as the blood treatment unit, in which negative depletion (using magnetic beads coated with anti-CD45 (MB-CD45) for removal of white blood cells (WBCs)) and positive enrichment using magnetic beads coated with the present compound (MB-SCH45) or the anti-EpCAM (MB-anti-EpCAM) were carried out. The second micromixer (II in FIG. 1A) served as the immunofluorescence staining chamber.

Capturing Cholangio-Cancerous Cells Using the Microfluidic Chip

The microfluidic chip constructed above was employed to capture cholangio-cancerous cells from healthy or CCA positive patient blood. Briefly, the blood samples collected from 65 CCA patients was independently mixed with red blood cell (RBC) lysis buffer and dispensed into 5 inlets in the topmost PDMS layer of the chip (L1 in FIG. 1A), then magnetic beads coated with the compound of formula (I) or anti-EpCAM were manually pipetted into the blood treatment unit, and gently mixed for 15 min. After incubation, the cells were identified and bound by the magnetic beads pre-coated with the compound of formula (I) of the present invention. Then, these magnetic beads-cells complexes were collected with a magnetic force and washed by 1×PBS buffer, and transferred to immunofluorescence staining unit of the chip for further analysis.

Statistical Analysis: The sample size (n) has been presented in the pertinent figure legends. Details regarding data normalization (for before and after chemotherapy patients) have been described in the Experimental Section. Statistical analysis was performed using OriginPro (OriginLab, Massachusetts, USA).

Example 1 Chemical Synthesis of the Present Compound

The present compounds were respectively synthesized in accordance with steps as described in schemes 1 to 5. In general, tetrasaccharide backbones were assembled in a [2+2] fashion from the appropriate disaccharide building blocks and convergent [4+4] glycosylation provided the fully protected octasaccharide skeleton, which was further subjected to functional group transformations to yield final compound with varying levels of O-sulfonation states. The glycan molecule was then biotinylated such that the resulting compound 20 (i.e., SCH45), could be conjugated onto the surface of streptavidin-coated Dynabeads.

The structure of the present synthetic glycosaminoglycan (GAC) is composed of four variably sulfated disaccharide units, with each sugar in the disaccharide unit being any one of an N-acetyl-α-D-glucosamine (α-D-GlcMAc, abbreviated as "N"), a β-D-glucuronic acid (β-D-GlcA, abbreviated as "G") or an a-L-iduronic acid (α-D-IdoA, abbreviated as "I"), and linked with another sugar by a-1→4 linkage. Thus, the present compound 20 may be represented as NINGNING.

Scheme 1: Synthesis of NI Disaccharide Donor

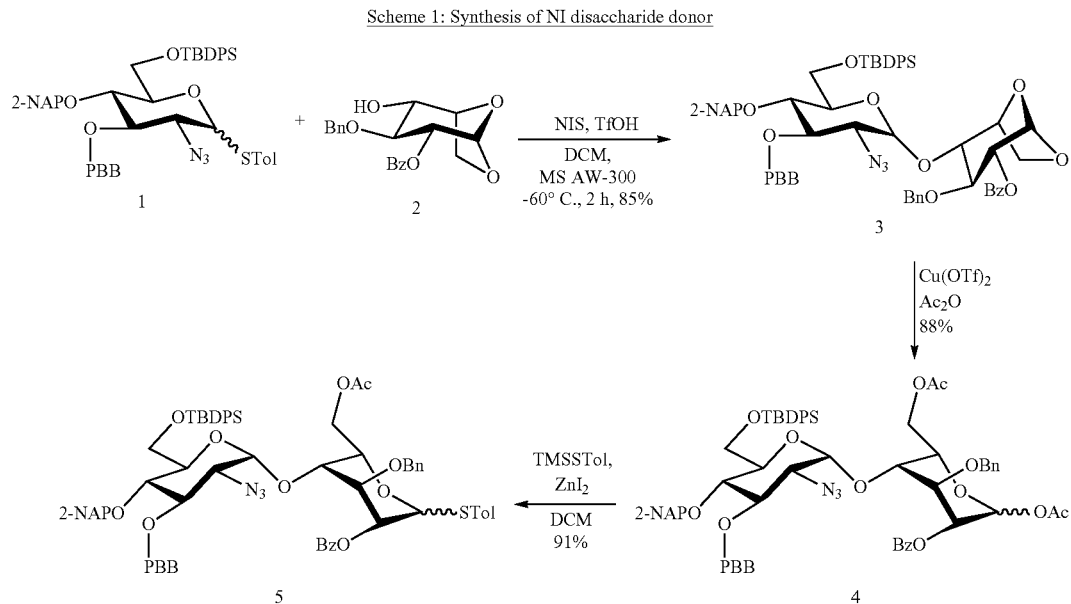

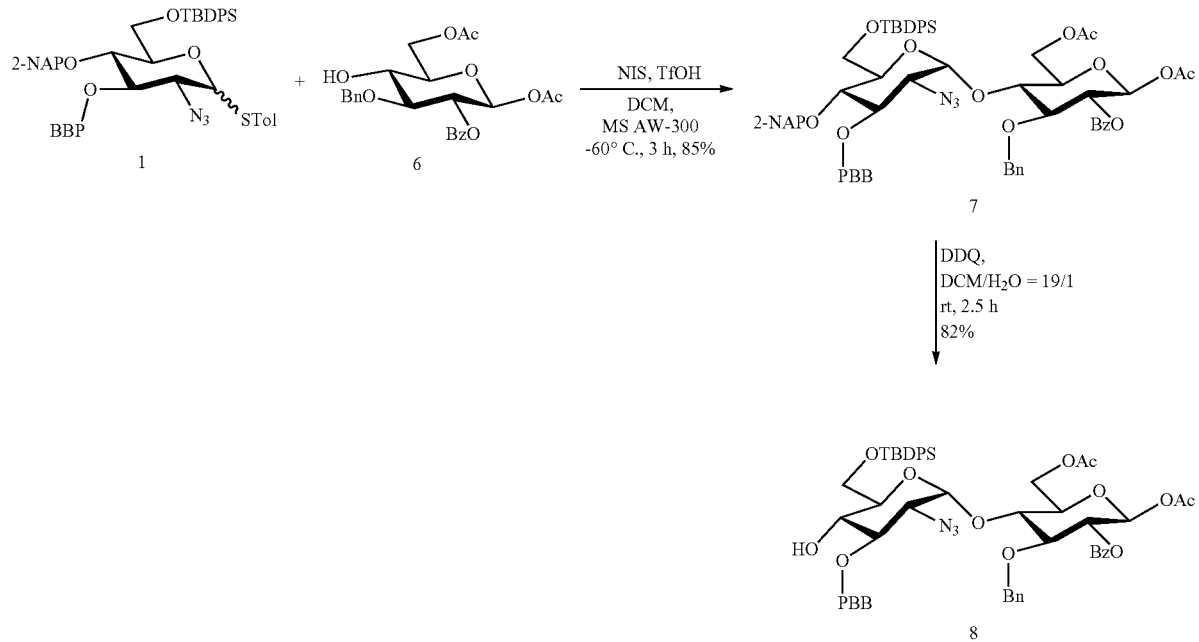

-continued
Scheme 3: Synthesis of NING tetrasaccharide skeleton
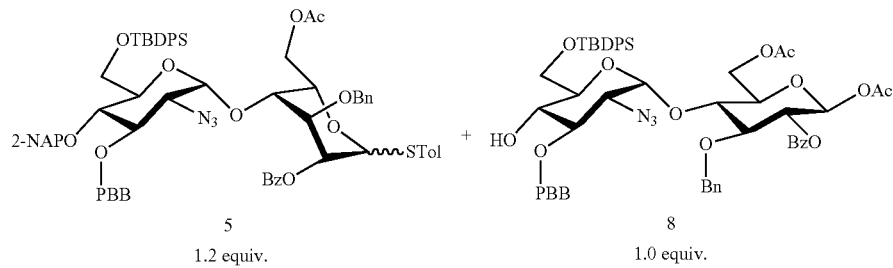
Scheme 4: Synthesis of NING tetrasaccharide donor and acceptor
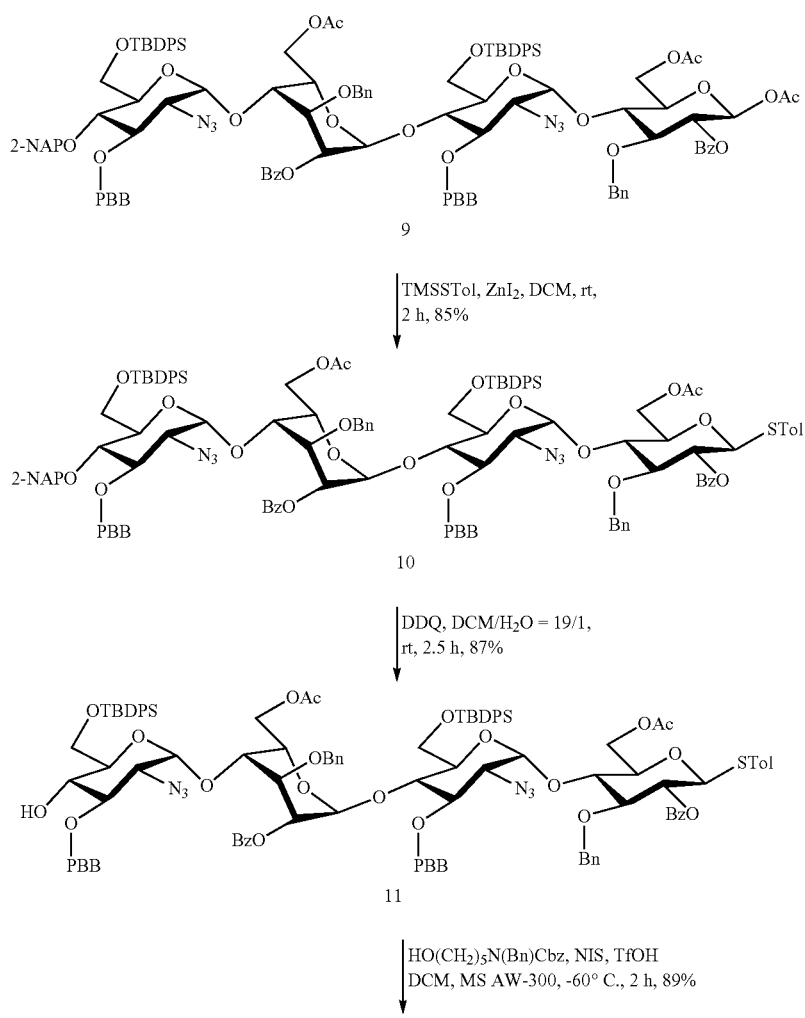

-continued
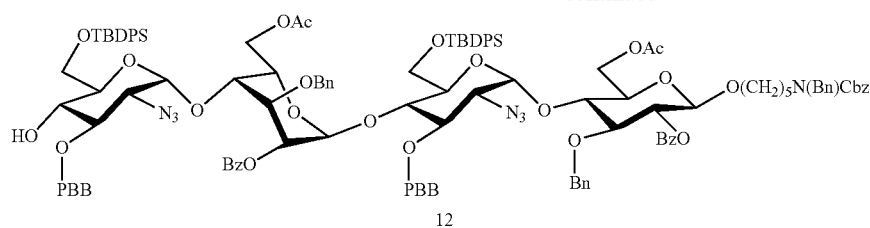
12
Scheme 5: Synthesis of NINGNING octasaccharide skeleton
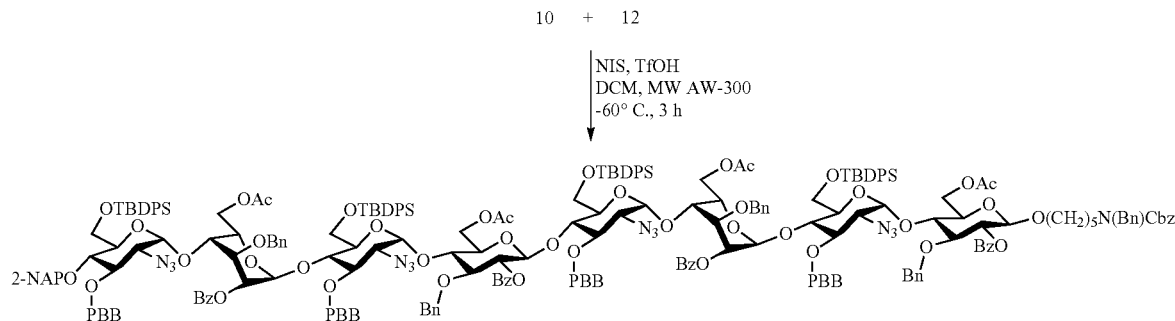
Scheme 6: Synthesis of the present compound
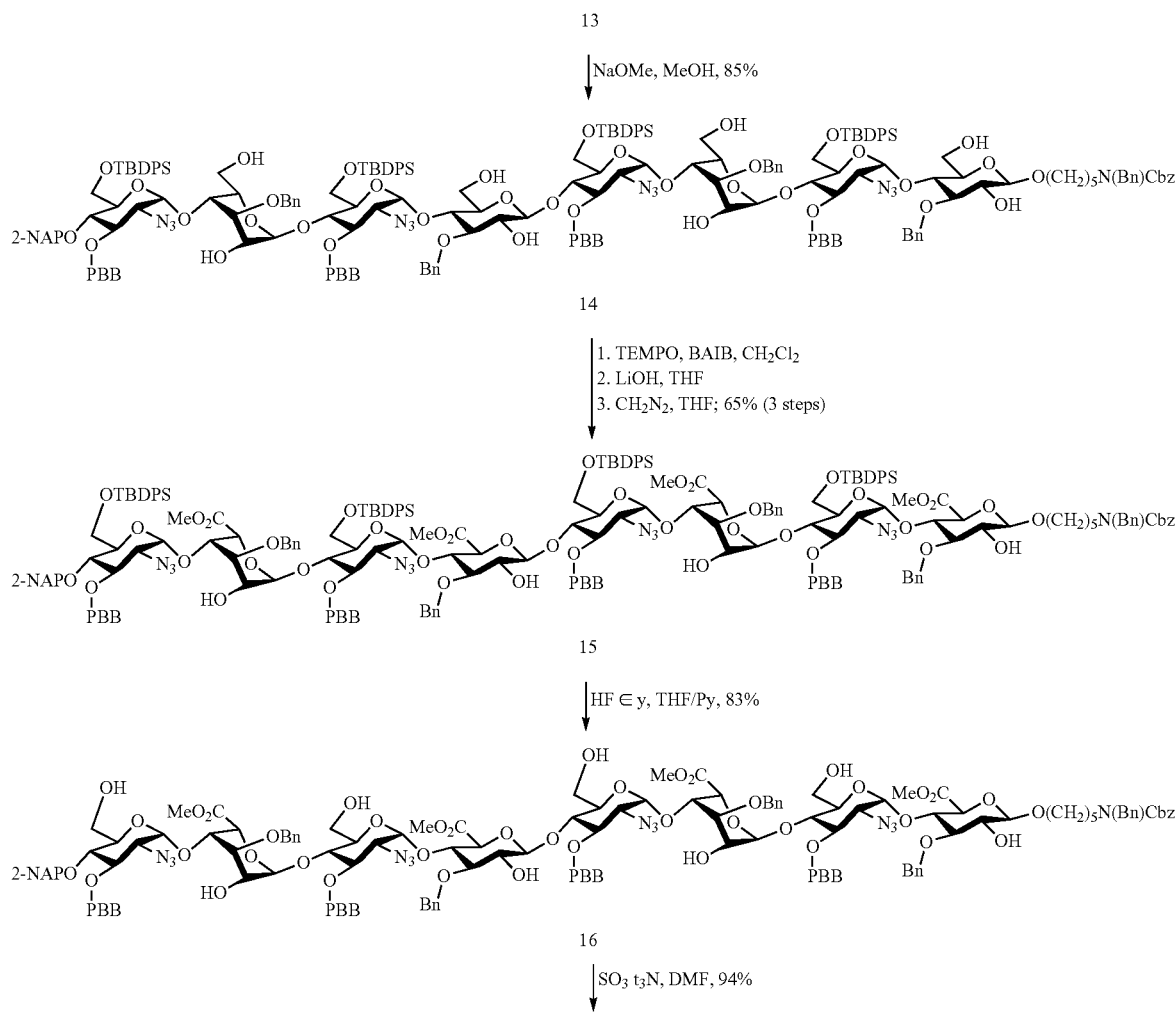

-continued
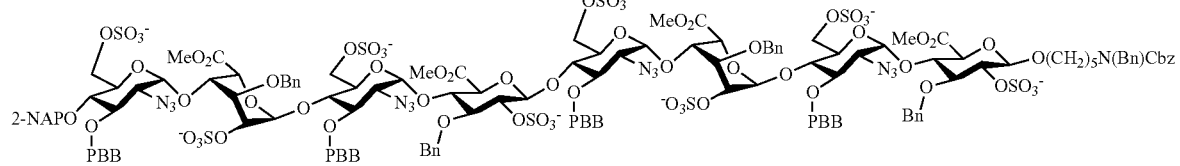
17
↓ LiOH, MeOH, CHCl₃, H₂O, 96%
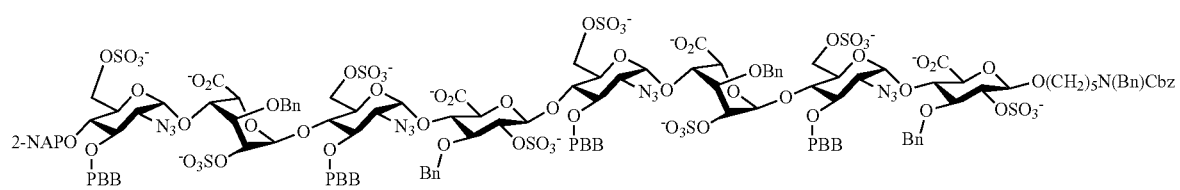
18
↓ Pd(OH)₂/C, MeOH, Phosphate buffer
H₂(g), 80%
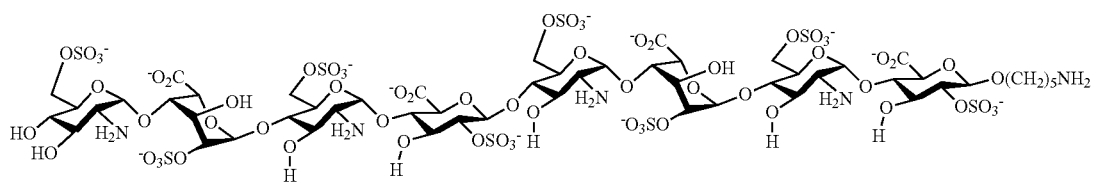
19
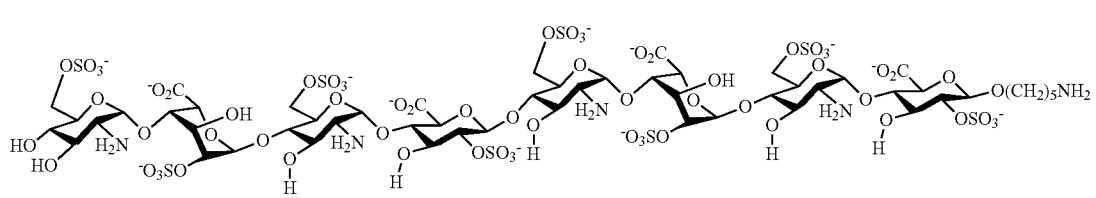
19
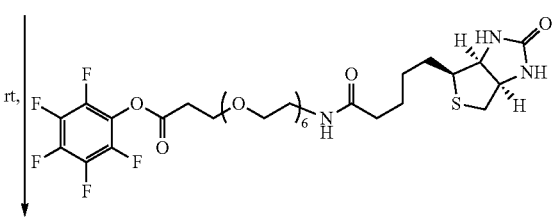
↓ Et₃N, DMF, rt,
20 h 94%

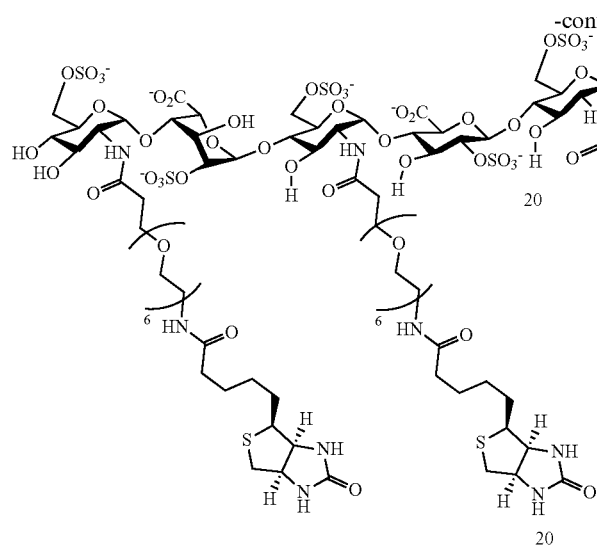
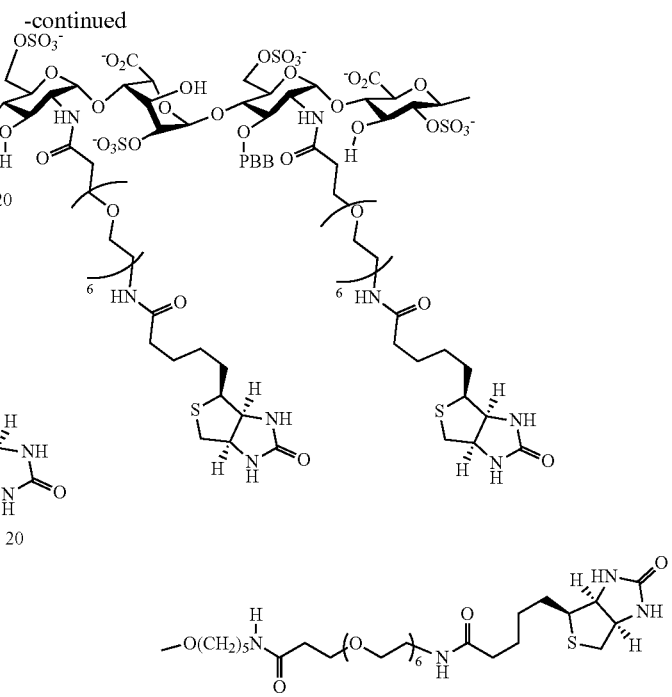

6-O-Acetyl-4-O-[2-azido-3-O-(4-bromobenzyl)-6-O-tert-butyldiphenylsilyl-2-deoxy-4-O-(2-naphthylmethyl)-α-D-glucopyranosyl]-2-O-benzoyl-3-O-benzyl-β-D-glucopyranosyl acetate (7)

A solution of the thioglycoside 1 (193 mg, 0.22 mmol) and the 4-alcohol 6 (86 mg, 0.19 mmol) in anhydrous CH$_2$Cl$_2$ (5.6 mL) with freshly dried 3 Å molecular sieves (557 mg) was stirred at room temperature for 1 h under argon. The reaction flask was cooled down to −60° C., N-idosuccinimide (NIS, 61 mg, 0.26 mmol) and triflic acid (TfOH, 3 µL, 0.04 mmol) were added to the solution, and the mixture was gradually warmed up to −50° C. After stirring for 2 h, the reaction was quenched by addition of Et$_3$N (8 µL, 0.06 mmol) was added to quench the reaction, the mixture was filtered through Celite, and the solid was washed by CH$_2$Cl$_2$. The filtrate was washed with 10% Na$_2$S$_2$O$_{5(aq)}$ (5.0 mL), dried over MgSO$_4$, filtered and concentrated under reduced pressure to furnish a residue, which was purified by flash column chromatography (ethyl acetate/hexane=1/4) to give the expected disaccharide 34 (192 mg, 86%). [α]$^{25}_D$+ 0.6 (c 5.34, CHCl$_3$); IR (thin film): ν 2930, 2107, 1738, 1265, 1111, 1067 cm$^{-1}$; $^1$H NMR (600 MHz, CDCl$_3$): δ 8.02 (d, J=7.6 Hz, 2H, Bz-H), 7.85-7.81 (m, 1H, Ar—H), 7.79-7.75 (m, 2H, Ar—H), 7.66 (d, J=7.1 Hz, 2H, Ar—H), 7.64-7.61 (m, 3H, Ar—H), 7.58 (t, J=7.4 Hz, 1H, Ar—H), 7.51-7.47 (m, 2H, Ar—H), 7.45 (t, J=7.8 Hz, 2H, Ar—H), 7.42 (d, J=8.2 Hz, 2H, Ar—H), 7.40-7.34 (m, 2H, Ar—H), 7.34-7.30 (m, 2H, Ar—H), 7.30-7.24 (m, 5H, Ar—H), 7.24-7.20 (m, 3H, Ar—H), 7.18 (d, J=8.2 Hz, 2H, Ar—H), 5.83 (d, J=7.9 Hz, 1H, 1-H), 5.52 (d, J=3.6 Hz, 1H, 1'-H), 5.43 (dd, J=7.9, 8.5 Hz, 1H, 2-H), 4.95-4.88 (m, 2H, ArCH$_2$), 4.85-4.80 (m, 2H, ArCH$_2$), 4.76 (d, J=10.7 Hz, 1H, ArCH$_2$), 4.73 (d, J=10.7 Hz, 1H, ArCH$_2$), 4.35 (d, J=12.3 Hz, 1H, 6-H$_a$), 4.09 (dd, J=12.3, 4.1 Hz, 1H, 6-H$_b$), 4.04 (dd, J=8.5, 8.5 Hz, 1H, 3-H), 4.02-3.80 (m, 1H, 6'-H$_a$), 3.95 (dd, J=9.0, 8.5 Hz, 1H, 4-H), 3.92-3.88 (m, 2H, 3'-H, 5'-H), 3.81-3.77 (m, 1H, 5-H), 3.75 (d, J=11.7 Hz, 1H, 6'-H$_b$), 3.62 (d, J=6.8 Hz, 1H, 4'-H), 3.32-3.25 (m, 1H, 2'-H), 1.99 (s, 3H, Ac), 1.74 (s, 3H, Ac), 1.04 (s, 9H, tBu TBDPS); $^{13}$C NMR (150 MHz, CDCl$_3$): δ 170.4 (C), 169.2 (C), 165.0 (C), 137.3 (C), 136.7 (C), 135.9 (CH), 135.5 (CH), 135.3 (C), 133.6 (CH), 133.3 (CH), 133.2 (CH), 133.0 (CH), 132.8 (C), 131.5 (CH), 129.8 (CH), 129.7 (CH), 129.5 (CH), 129.1 (C), 128.6 (CH), 128.4 (CH), 128.2 (CH), 127.9 (CH), 127.8 (CH), 127.75 (CH), 127.70 (CH), 127.6 (CH), 126.3 (CH), 126.2 (CH), 126.0 (CH), 125.5 (CH), 121.8 (C), 97.9 (CH), 91.7 (CH), 82.9 (CH), 79.9 (CH), 78.0 (CH), 75.2 (CH$_2$), 74.6 (CH$_2$), 74.5 (CH$_2$), 73.4 (CH), 73.2 (CH), 73.0 (CH), 72.6 (CH), 63.3 (CH), 62.6 (CH$_2$), 62.0 (CH$_2$), 26.9 (CH$_3$), 20.8 (CH$_3$), 20.4 (CH$_3$), 19.3 (C); HRMS ESI: m/z calcd for C$_{64}$H$_{66}$N$_3$O$_{13}$BrSiNa ([M+Na]$^+$): 1214.3446, found: 1214.3455.

[2-Azido-3-O-(4-bromobenzyl)-6-O-tert-butyldiphenylsilyl-2-deoxy-4-O-(2-naphthylmethyl)-α-D-glucopyranosyl]-(1→4)-(6-O-acetyl-2-O-benzoyl-3-O-benzyl-α-L-idopyranosyl)-(1→4)-[2-azido-3-O-(4-bromobenzyl)-6-O-tert-butyldiphenylsilyl-2-deoxy-α-D-glucopyranosyl]-(1→4)-6-O-acetyl-2-O-benzoyl-3-O-benzyl-β-D-glucopyranosyl acetate (9)

A solution of the thioglycoside 5 (1.2 equiv.) and the 4'-alcohol 8 (1.0 equiv.) in anhydrous CH$_2$Cl$_2$ (10 mL/total grams of the thioglycoside and the 4'-alcohol) with freshly activated AW-300 molecular sieves (0.5 g/total grams of the thioglycoside and the 4'-alcohol) was stirred at room temperature for 1 h and then cooled to −78° C. NIS (2.0 equiv.) was added to this mixture, and after 5 min, TfOH (0.1 equiv.) was added slowly through a microsyringe. The temperature was gradually raised to −50° C. and kept at this temperature until the complete consumption of the thioglycoside 5 by TLC plate analysis (about 2 h). Then the mixture was neutralized by addition of Et$_3$N, diluted with CH$_2$Cl$_2$ and filtered through Celite. The resulting solution was washed with a 10% Na$_2$S$_2$O$_{3(aq)}$ and H$_2$O. The organic layer was combined, dried over MgSO$_4$ and concentrated under reduced pressure. The residue was purified by flash column chromatography to yield the tetrasaccharides 9 (81%).

IR (thin film): ν 2930, 2108, 1742, 1266, 1111 cm$^{-1}$; $^1$H NMR (600 MHz, CDCl$_3$): δ 8.03 (dd, J=8.2, 1.0 Hz, 2H, Bz-H), 8.00 (dd, J=7.8, 1.1 Hz, 2H, Bz-H), 7.84 (dd, J=6.1, 3.1 Hz, 1H 2-NAP-H), 7.78-7.72 (m, 2H, Ar—H), 7.69-7.61 (m, 4H, Ar—H), 7.60-7.54 (m, 6H, Ar—H), 7.51-7.43 (m, 4H, Ar—H), 7.41-7.29 (m, 13H, Ar—H), 7.28-7.13 (m, 17H, Ar—H), 7.05 (d, J=8.3 Hz, 1H, Ar—H), 7.00 (d, J=8.3 Hz, 1H, Ar—H), 5.83 (d, J=8.0 Hz, 1H, 1-H), 5.44-5.39 (m, 3H, 1'-H, 1"-H, 2-H), 5.17 (s, 1H, 2"-H), 4.90 (d, J=11.3 Hz, 1H, ArCH$_2$), 4.89 (d, J=10.8 Hz, 1H, ArCH$_2$), 4.84 (s, 2H, ArCH$_2$), 4.78 (d, J=10.3 Hz, 1H, ArCH$_2$), 4.73-4.70 (m, 2H, ArCH$_2$), 4.69 (d, J=3.6 Hz, 1H, 1'''-H), 4.48 (d, J=11.3 Hz, 1H, ArCH$_2$), 4.39-4.33 (m, 3H, ArCH$_2$, 6-H$_a$, 5"-H), 4.17 (dd, J=9.6, 8.8 Hz, 1H, 4'-H), 4.15-4.08 (m, 3H, ArCH$_2$, 3"-H, 6"-H$_a$), 4.05-3.99 (m, 3H, 3-H, 6'-H$_a$, 6"-H$_b$), 3.96 (dd, J=12.1, 4.3 Hz, 1H, 6-H$_b$), 3.89-3.80 (m, 4H, 4-H, 6'-H$_b$, 4'''-H, 6'''-H$_a$), 3.77 (ddd, J=9.3, 3.8, 2.1 Hz, 1H, 5-H), 3.74-3.70 (m, 2H, 3'-H, 5'''-H), 3.68-3.63 (m, 2H, 3'''-H, 6'''-H$_b$), 3.55 (s, 1H, 4"-H), 3.51 (d, J=9.6 Hz, 1H, 5'-H), 3.29 (dd, J=10.2, 3.5 Hz, 1H, 2'''-H), 3.18 (dd, J=10.3, 4.0 Hz, 1H, 2'-H), 1.99 (s, 3H, Ac), 1.73 (s, 3H, Ac), 1.68 (s, 3H, Ac), 1.05 (s, 9H, tBu), 0.96 (s, 9H, tBu); $^{13}$C NMR (150 MHz, CDCl$_3$): δ 170.1 (C), 170.0 (C), 169.1 (C), 165.5 (C), 164.9 (C), 137.3 (C), 137.2 (C), 137.0 (C), 136.7 (C), 135.8 (CH), 135.57 (CH), 135.55 (CH), 135.4 (C), 133.5 (CH), 133.3 (C), 133.2 (C), 133.1 (C), 133.0 (CH), 132.98 (C), 132.92 (C), 131.4 (C), 132.8 (C), 131.4 (CH), 131.0 (CH), 129.8 (CH), 129.7 (CH), 129.6 (CH), 129.5 (CH), 129.4 (CH), 129.0 (C), 128.9 (CH), 128.6 (CH), 128.59 (CH), 128.52 (CH), 128.3 (CH), 128.15 (CH), 128.09 (CH), 127.85 (CH), 127.81 (CH), 127.71 (CH), 127.67 (CH), 127.57 (CH), 127.50 (CH), 127.3 (CH), 126.3 (CH), 126.1 (CH), 125.9 (CH), 125.7 (CH), 121.6 (C), 121.1 (C), 98.4 (CH), 97.4 (CH), 97.0 (CH), 91.7 (CH), 82.9 (CH), 80.3 (CH), 78.5 (CH), 77.7 (CH), 75.1 (CH$_2$), 74.4 (CH$_2$), 74.2 (CH$_2$), 74.1 (CH$_2$), 73.8 (CH), 73.4 (CH), 73.0 (CH), 72.8 (CH, CH$_2$), 72.64 (CH), 72.59 (CH), 72.55 (CH), 68.4 (CH), 64.8 (CH), 63.9 (CH), 63.6 (CH), 62.3 (CH$_2$), 62.2 (CH$_2$), 62.0 (CH$_2$), 26.8 (CH$_3$), 26.7 (CH$_3$), 20.8 (CH$_3$), 20.6 (CH$_3$), 20.3 (CH$_3$), 19.36 (C), 19.30 (C); HRMS (MALDI): m/z calcd for C$_{115}$H$_{120}$Br$_2$N$_6$O$_{24}$Si$_2$Na ([M+Na]$^+$): 2209.2178, found: 2209.2236.

4-Methylphenyl [2-azido-3-O-(4-bromobenzyl)-6-O-tert-butyldiphenylsilyl-2-deoxy-4-O-(2-naphthyl methyl)-α-D-glucopyranosyl]-(1→4)-(6-O-acetyl-2-O-benzoyl-3-O-benzyl-α-L-idopyranosyl)-(1→4)-[2-azido-3-O-(4-bromobenzyl)-6-O-tert-butyldiphenylsilyl-2-deoxy-α-D-glucopyranosyl]-(1→4)-6-O-acetyl-2-O-benzoyl-3-O-benzyl-1-thio-3-D-glucopyranoside (10)

Trimethyl(4-methylphenylthio)silane (TMSSTol, 0.08 mL, 0.39 mmol) and ZnI$_2$ (0.13 g, 0.41 mmol) were added to a solution of compound 9 (0.43 g, 0.196 mmol) in anhydrous CH$_2$Cl$_2$ (5 mL) at ambient temperature under argon. After the tetrasaccharide was consumed completely (2 h), the mixture was diluted with CH$_2$Cl$_2$ (8 mL) and then filtered out. The filtrate was washed with satd. NaHCO$_{3(aq)}$, dried over MgSO$_4$ and filtered. The resulting solution was concentrated under reduced pressure and purified by flash column chromatography (ethyl acetate/hexane=1/5) to provide the thioglycoside 10 (0.38 g, 85%). IR (thin film): ν 2927, 2108, 1733, 1266, 1112, 708 cm$^{-1}$; $^1$H NMR (600 MHz, CDCl$_3$): δ 8.09 (dd, J=7.9, 1.0 Hz, 2H, Bz-H), 7.99 (d, J=8.1, 1.5 Hz, 2H, Bz-H), 7.84 (dd, J=6.0, 3.4 Hz, 1H, 2-NAP-H), 7.77-7.72 (m, 2H, Ar—H), 7.68-7.52 (m, 10H, Ar—H), 7.51-7.44 (m, 4H, Ar—H), 7.41-7.12 (m, 33H, Ar—H), 7.08-6.98 (m, 6H, Ar—H), 5.43 (d, J=4. Hz, 1H, 1'-H), 5.40 (s, 1H, 1"-H), 5.24 (dd, J=9.7, 8.7 Hz, 1H, 2-H), 5.19 (s, 1H, 2"-H), 4.90 (d, J=11.3 Hz, 1H, ArCH$_2$), 4.89 (d, J=11.0 Hz, 1H, ArCH$_2$), 4.84 (s, 2H, ArCH$_2$), 4.75-4.65 (m, 5H, ArCH$_2$, 1-H, 1'''-H), 4.49-4.44 (m, 2H, ArCH$_2$, 6-H$_a$), 4.38-4.33 (m, 2H, ArCH$_2$, 5'''-H), 4.17-4.09 (m, 4H, ArCH$_2$, 4'-H, 3"-H, 6"-H$_a$), 4.05-4.00 (m, 2H, 5'''-H, 6'''-H$_a$), 3.95 (dd, J=8.3, 8.7 Hz, 1H, 3-H), 3.90 (dd, J=11.9, 4.7 Hz, 1H, 6-H$_b$), 3.88-3.80 (m, 3H, 6"-H$_b$, 4'''-H, 6'''-H$_a$), 3.74-3.63 (m, 5H, 4-H, 3'-H, 3'''-H, 6'-H$_b$, 6'''-H$_b$), 3.60 (ddd, J=9.8, 4.8, 2.4 Hz, 1H, 5-H), 3.55 (s, 1H, 4"-H), 3.48 (d, J=9.7 Hz, 1H, 5'-H), 3.29 (dd, J=10.2, 3.5 Hz, 1H, 2'''-H), 3.15 (dd, J=10.3, 4.1 Hz, 1H, 2'-H), 2.32 (s, 3H, SPhCH$_3$), 1.72 (s, 3H, Ac), 1.69 (s, 3H, Ac), 1.05 (s, 9H, tBu), 0.95 (s, 9H, tBu); $^{13}$C NMR (150 MHz, CDCl$_3$): δ 170.1 (C), 170.0 (C), 165.6 (C), 165.5 (C), 165.1 (C), 138.3 (C), 137.4 (C), 137.3 (C), 137.1 (C), 136.7 (C), 135.83 (CH), 135.82 (CH), 135.57 (CH), 135.54 (CH), 135.4 (C), 133.7 (CH), 133.4 (CH), 133.31 (C), 133.27 (CH), 133.2 (C), 133.1 (CH), 133.92 (C), 133.88 (C), 131.4 (C), 131.0 (CH), 129.81 (CH), 129.79 (CH), 129.70 (CH), 129.67 (CH), 129.61 (C), 129.59 (CH), 129.57 (C), 128.9 (CH), 128.6 (CH), 128.53 (CH), 128.51 (CH), 128.3 (CH), 128.16 (C), 128.12 (CH), 128.09 (CH), 127.9 (CH), 127.71 (CH), 127.67 (CH), 127.60 (CH), 127.57 (CH), 127.5 (CH), 127.4 (CH), 126.4 (CH), 126.2 (CH), 126.0 (CH), 125.7 (CH), 121.6 (C), 121.1 (C), 98.5 (CH), 97.4 (CH), 97.0 (CH), 85.9 (CH), 84.7 (CH), 80.3 (CH), 78.6 (CH), 77.7 (CH), 76.4 (CH), 75.1 (CH$_2$), 74.6 (CH$_2$), 74.2 (CH$_2$), 73.9 (CH), 73.1 (CH), 72.91 (CH), 72.86 (CH, CH$_2$), 72.7 (CH), 72.6 (CH), 68.6 (CH), 64.9 (CH), 63.9 (CH), 63.5 (CH), 62.6 (CH$_2$), 62.3 (CH$_2$), 62.1 (CH$_2$), 62.0 (CH$_2$), 26.9 (CH$_3$), 26.8 (CH$_3$), 21.1 (CH$_3$), 20.6 (CH$_3$), 20.4 (CH$_3$), 19.4 (C), 19.3 (C); HRMS (MALDI): m/z calcd for C$_{120}$H$_{124}$Br$_2$N$_6$O$_{22}$SSi$_2$Na ([M+Na]$^+$): 2273.3711, found: 2273.3777.

4-Methylphenyl [2-azido-3-O-(4-bromobenzyl)-6-O-tert-butyldiphenylsilyl-2-deoxy-α-D-glucopyranosyl]-(1→4)-(6-O-acetyl-2-O-benzoyl-3-O-benzyl-α-L-idopyrano-syl)-(1→4)-[2-azido-3-O-(4-bromobenzyl)-6-O-tert-butyldiphenylsilyl-2-deoxy-α-D-glucopyranosyl]-(1→4)-6-O-acetyl-2-O-benzoyl-3-O-benzyl-1-thio-3-D-glucopyranoside (11)

To a solution of the thioether-linked tetrasaccharide 10 (0.38 g, 0.17 mmol) in a mixed solvent (CH$_2$Cl$_2$/H$_2$Ø=19/1, 11.4 mL) was added DDQ (0.06 g, 0.26 mmol) at room temperature. After stirring for 2 h, the reaction was quenched by addition of 10% Na$_2$S$_2$O$_{3(aq)}$, and the organic mixture was extracted with CH$_2$Cl$_2$. The organic layers were consecutively washed with satd. NaHCO$_{3(aq)}$ and H$_2$O, dried over anhydrous MgSO$_4$, filtered and concentrated under reduced pressure. The residue was purified by flash column chromatography (ethyl acetate/hexane=1/5) to give the 4'''-alcohol 11 (0.31 g, 87%). IR (thin film): ν 2929, 2108, 1733, 1265, 1112, 708 cm$^{-1}$; $^1$H NMR (600 MHz, CDCl$_3$): δ 8.08 (d, J=7.8 Hz, 2H, Bz-H), 8.02 (d, J=7.9 Hz, 2H, Bz-H), 7.67-7.55 (m, 9H, Ar—H), 7.49-7.39 (m, 7H, Ar—H), 7.39-7.25 (m, 17H, Ar—H), 7.23-6.15 (m, 9H, Ar—H), 7.12-7.04 (m, 6H, Ar—H), 5.44 (d, J=4.0 Hz, 1H, 1'-H), 5.42 (s, 1H, 1"-H), 5.23 (dd, J=9.8, 9.1 Hz, 1H, 2-H), 5.19 (s, 1H, 2"-H), 4.90 (d, J=11.6 Hz, 1H, ArCH$_2$), 4.84 (d, J=11.1 Hz, 1H, ArCH$_2$), 4.75-4.65 (m, 5H, 1-H, 1'''-H, ArCH$_2$), 4.49 (d, J=11.3 Hz, 2H, ArCH$_2$), 4.45 (d, J=10.6 Hz, 1H, 6-H$_a$), 4.36 (td, J=6.5, 2.2 Hz, 1H, 5''-H), 4.20 (d, J=11.1 Hz, 1H, ArCH$_2$), 4.15 (dd, J=9.8, 9.2 Hz, 1H, 4'-H), 4.11-4.02 (m, 3H, 6'-H$_a$, 3''-H, 6'''-H$_a$), 3.94 (dd, J=8.8, 8.3 Hz, 1H, 3-H), 3.92-3.84 (m, 3H, 6-H$_b$, 6''-H$_a$, 6'''-H$_a$), 3.75-3.64 (m, 6H, 4-H, 3'-H, 6'-H$_b$, 4'''-H, 5'''-H, 6'''-H$_b$), 3.59 (ddd, J=9.3, 4.2, 2.0 Hz, 1H, 5-H), 3.57-3.53 (m, 2H, 4''-H, 3'''-H), 3.46-3.50 (m, 1H, 5'-H), 3.18-3.14 (m, 2H, 2'-H, 2'''-H), 2.32 (s, 3H, SPhCH$_3$), 1.79 (s, 3H, Ac), 1.68 (s, 3H, Ac), 1.04 (s, 9H, tBu), 0.99 (s, 9H, tBu); $^{13}$C NMR (150 MHz, CDCl$_3$): δ 170.2 (C), 170.1 (C), 165.5 (C), 165.1 (C), 138.3 (C), 137.32 (C), 137.31 (C), 137.1 (C), 137.0 (C), 135.9 (CH), 135.60 (CH), 135.58 (CH), 135.5 (CH), 133.7 (CH), 133.4 (CH), 133.2 (CH), 132.9 (C), 132.8 (CH), 132.7 (C), 131.4 (C), 131.1 (CH), 129.93 (CH), 129.91 (CH), 129.84 (CH), 129.83 (CH), 129.7 (CH), 129.63 (CH), 129.60 (CH), 129.5 (CH), 129.0 (CH), 128.6 (CH), 128.5 (CH), 128.43 (CH), 128.14 (C), 128.09 (CH), 127.84 (CH), 127.78 (CH), 127.74 (CH), 127.63 (CH), 127.56 (CH), 127.4 (CH), 121.7 (C), 121.1 (C), 98.3 (CH), 97.4 (CH), 97.0 (CH), 85.9 (CH), 84.8 (CH), 79.9 (CH), 78.5 (CH), 76.4 (CH), 74.6 (CH$_2$), 74.2 (CH$_2$), 74.1 (CH$_2$), 73.7 (CH), 73.1 (CH), 72.93 (CH), 72.91 (CH), 72.88 (CH$_2$), 72.6 (CH), 72.3 (CH), 71.9 (CH), 68.8 (CH), 65.3 (CH), 63.7 (CH$_2$), 63.5 (CH), 63.0 (CH), 62.5 (CH$_2$), 62.2 (CH$_2$), 62.1 (CH$_2$), 26.9 (CH$_3$), 26.8 (CH$_3$), 21.1 (CH$_3$), 20.7 (CH$_3$), 20.4 (CH$_3$), 19.4 (C), 19.2 (C); HRMS (MALDI): m/z calcd for C$_{109}$H$_{116}$Br$_2$N$_6$O$_{22}$SSi$_2$Na ([M+Na]$^+$): 2133.1855, found: 2133.1912.

N-Benzyl-N-benzyloxycarbonyl-5-aminopentyl [2-azido-3-O-(4-bromobenzyl)-6-O-tert-butyldiphenylsilyl-2-deoxy-α-D-glucopyranosyl]-(1→4)-(6-O-acetyl-2-O-benzoyl-3-O-benzyl-α-L-idopyranosyl)-(1→4)-[2-azido-3-O-(4-bromobenzyl)-6-O-tert-butyldiphenylsilyl-2-deoxy-α-D-glucopyranosyl]-(1→4)-6-O-acetyl-2-O-benzoyl-3-O-benzyl-β-D-glucopyranoside (12)

A solution of the thioglycoside 11 (0.78 g, 0.37 mmol) and N-benzyl-N-benzyloxycarbonyl-5-aminopentanol[4] (0.12 g, 0.37 mmol) in CH$_2$Cl$_2$ (10 mL) with freshly dried AW-300 molecular sieves (1 g) was stirred at room temperature for 1 h under N$_2$. The reaction flask was cooled to −78° C., NIS (0.08 g) and TfOH (27 μmL) were added to the solution, and the mixture was gradually warmed up to room temperature. After the thioglycoside was consumed completely according to TLC plate analysis (2 h), Et$_3$N was added to quench the reaction, the mixture was filtered through Celite, and the solid was washed by CH$_2$Cl$_2$. The filtrate was washed with 10% Na$_2$S$_2$O$_{3(aq)}$, dried over MgSO$_4$ and concentrated under reduced pressure to furnish a residue, which was purified by flash column chromatography (ethyl acetate/hexane=1/3) to give the expected tetrasaccharide 12 (0.76 g, 89%). IR (thin film): ν 2926, 2108, 1737, 1266, 1112, 701 cm$^{-1}$; $^1$H NMR (600 MHz, CDCl$_3$): δ 8.03-7.97 (m, 4H, Bz-H), 7.67-7.62 (m, 4H, Ar—H), 7.61-7.55 (m, 4H, Ar—H), 7.50-7.39 (m, 6H, Ar—H), 7.38-7.26 (m, 23H, Ar—H), 7.26-7.20 (m, 7H, Ar—H), 7.20-7.15 (m, 6H, Ar—H), 7.11-7.05 (m, 5H, Ar—H), 5.48 (d, J=3.7 Hz, 1H, 1'-H), 5.42 (s, 1H, 1''-H), 5.25 (t, J=8.3 Hz, 1H, 2-H), 5.19 (s, 1H, 2''-H), 5.12 (d, J=7.4 Hz, 2H, ArCH$_2$), 4.91 (d, J=11.6 Hz, 1H, ArCH$_2$), 4.84 (d, J=11.2 Hz, 1H, ArCH$_2$), 4.75-4.65 (m, 4H, ArCH$_2$, 1''-H), 4.53-4.43 (m, 3H, ArCH$_2$, 1-H), 4.41-4.32 (m, 4H, ArCH$_2$, 6-H$_a$, 5''-H), 4.21-4.14 (m, 2H, ArCH$_2$, 4'-H), 4.11-4.02 (m, 3H, 6'-H$_a$, 3''-H, 6''-H$_a$), 3.99- 3.88 (m, 3H, 3-H, 6-H$_b$, 6'''-H$_a$), 3.85 (d, J=12.0 Hz, 6''-H$_b$), 3.77 (t, J=9.0 Hz, 1H, 4-H), 3.75-3.66 (m, 5H, 3'-H, 6'-H$_b$, 4'''-H, 5'''-H, 6'''-H$_b$), 3.66-3.61 (m, 1H), 3.58-3.48 (m, 4H, 5-H, 5'-H, 3'''-H), 3.39-3.26 (m, 1H), 3.18-3.14 (m, 2H, 2'-H, 2'''-H), 3.08-2.89 (m, 2H), 2.46 (d, J=2.6 Hz, 1H, 4'''-OH), 1.79 (s, 3H, Ac), 1.66-1.59 (m, 2H), 1.63 (s, 3H, Ac), 1.50-1.25 (m, 4H), 1.03 (s, 9H, tBu), 0.98 (s, 9H, tBu); $^{13}$C NMR (150 MHz, CDCl$_3$): δ 170.2 (C), 170.1 (C), 165.5 (C), 165.0 (C), 156.6/156.0 (C), 137.9 (C), 137.8 (C), 137.4 (C), 137.3 (C), 137.1 (C), 137.0 (C), 136.8/136.7 (C), 135.9 (CH), 135.6 (CH), 135.56 (CH), 135.52 (CH), 133.3 (C), 133.2 (CH), 132.9 (C), 132.8 (C), 132.7 (C), 131.4 (CH), 131.1 (CH), 129.93 (CH), 129.91 (CH), 129.8 (CH), 129.7 (CH), 129.62 (CH), 129.60 (CH), 128.9 (CH), 128.56 (CH), 128.51 (CH), 128.45 (CH), 128.3 (CH), 128.1 (CH), 127.85 (CH), 127.78 (CH), 127.72 (CH), 127.61 (CH), 127.56 (CH), 127.4 (CH), 127.23 (CH), 127.17 (CH), 127.09 (CH), 121.6 (C), 121.1 (C), 100.8 (CH), 98.2 (CH), 97.2 (CH), 96.9 (CH), 83.3 (CH), 79.9 (CH), 78.5 (CH), 74.3 (CH$_2$), 74.2 (CH$_2$), 74.10 (CH$_2$), 73.96 (CH), 73.7 (CH), 73.1 (CH), 72.93 (CH), 72.88 (CH$_2$), 72.86 (CH), 72.6 (CH), 72.5 (CH$_2$), 72.3 (CH), 71.9 (CH), 69.7 (CH$_2$), 69.6 (CH$_2$), 68.8 (CH), 67.0 (CH$_2$), 65.3 (CH), 63.6 (CH$_2$), 63.5 (CH), 63.0 (CH), 62.5 (CH$_2$), 62.2 (CH$_2$), 62.1 (CH$_2$), 53.7 (CH$_2$), 50.4 (CH$_2$), 50.1 (CH$_2$), 47.0 (CH$_2$), 46.0 (CH$_2$), 21.7 (CH$_3$), 29.2 (CH$_3$), 28.9 (CH$_2$), 27.6/27.2 (CH$_2$), 26.9 (CH$_3$), 26.8 (CH$_3$), 23.0 (CH$_2$), 20.7 (CH$_3$), 20.3 (CH$_3$), 19.4 (C), 19.2 (C); HRMS (ESI): m/z calcd for C$_{122}$H$_{133}$Br$_2$N$_7$O$_{25}$Si$_2$Na ([M+Na]$^+$): 2332.7154, found: 2332.7119.

N-Benzyl-N-benzyloxycarbonyl-5-aminopentyl [2-azido-3-O-(4-bromobenzyl)-6-O-tert-butyldiphenylsilyl-2-deoxy-4-O-(2-naphthylmethyl)-α-D-glucopyranosyl]-(1→4)-(6-O-acetyl-2-O-benzoyl-3-O-benzyl-α-L-idopyranosyl)-(1→4)-[2-azido-3-O-(4-bromobenzyl)-6-O-tert-butyldiphenylsilyl-2-deoxy-α-D-glucopyranosyl]-(1→4)-(6-O-acetyl-2-O-benzoyl-3-O-benzyl-β-D-glucopyranosyl)-(1→4)-[2-azido-3-O-(4-bromobenzyl)-6-O-tert-butyldiphenylsilyl-2-deoxy-α-D-glucopyranosyl]-(1→4)-(6-O-acetyl-2-O-benzoyl-3-O-benzyl-α-L-idopyranosyl)-(1→4)-[2-azido-3-O-(4-bromobenzyl)-6-O-tert-butyldiphenylsilyl-2-deoxy-α-D-glucopyranosyl]-(1→4)-6-O-acetyl-2-O-benzoyl-3-O-benzyl-β-D-glucopyranoside (13)

A solution of the thioglycoside 10 (1.4 equiv.) and 4'''-alcohol 12 (1.0 equiv.) in anhydrous CH$_2$Cl$_2$ (10 mL/total grams of the thioglycoside and the 4'''-alcohol) with freshly activated AW-300 molecular sieves (0.5 g/total grams of the thioglycoside and the 4'''-alcohol) was stirred at room temperature for 1 h and then cooled to −40° C., followed by the addition of NIS (1.6 equiv.). After stirring for 5 min, TfOH (0.4 equiv.) was added to the solution slowly through a microsyringe. The reaction was warmed up to room temperature gradually and kept stirring until the complete consumption of the thioglycoside by TLC plate analysis (about 2 h). The mixture was neutralized by addition of Et$_3$N, diluted with CH$_2$Cl$_2$ and filtered through Celite. The resulting solution was washed with 10% Na$_2$S$_2$O$_{3(aq)}$ and H$_2$O. The organic layer was combined, dried over MgSO$_4$ and concentrated under reduced pressure. The residue was purified by flash column chromatography to yield octasaccharides 13 (72%).

[α]$^{26}_D$ −2.3 (c 5.0, CHCl$_3$); IR (thin film): ν 2928, 2108, 1741, 1698, 1264, 1112, 1038, 701 cm$^{-1}$; $^1$H NMR (600 MHz, CDCl$_3$): δ 8.02-7.97 (m, 4H, Bz-H), 7.96-7.92 (m, 2H, Bz-H), 7.85-7.82 (m, 1H, Ar—H), 7.81-7.78 (m, 2H, Ar—H), 7.76-7.71 (m, 3H, Ar—H), 7.69-7.64 (m, 4H, Ar—H), 7.63-7.60 (m, 2H, Ar—H), 7.58-7.47 (m, 15H, Ar—H), 7.44-7.40 (m, 2H, Ar—H), 7.40-7.33 (m, 14H, Ar—H), 7.33-7.18 (m, 44H, Ar—H), 7.18-7.09 (m, 12H, Ar—H), 7.07-6.97 (m, 8H, Ar—H), 5.46 (d, J=4.0 Hz, 1H, 1'-H), 5.44 (d, J=4.0 Hz, 1H, 1''''''-H), 5.41 (s, 1H, 1''-H), 5.29-5.21 (m, 3H, 2-H, 2''''-H, 1'''''-H), 5.18 (bs, 1H, 2''-H), 5.15 (dd, J=3.4, 2.8 Hz, 1H, 2''''''-H), 5.12 (d, J=7.9 Hz, 2H, PhCH$_2$ in Cbz), 4.91-4.84 (m, 4H, 1''''-H, ArCH$_2$), 4.83 (s, 2H, NaphCH$_2$), 4.79 (d, J=11.1 Hz, 1H, ArCH$_2$), 4.74-4.66 (m, 6H, 1'''-H, ArCH$_2$), 4.60 (d, J=3.5 Hz, 1H, 1'''''''-H), 4.53 (d, J=10.1 Hz, 1H, ArCH$_2$), 4.49-4.42 (m, 3H, 1-H, ArCH$_2$), 4.40-4.32 (m, 5H), 4.18-4.04 (m, 8H), 4.04-3.99 (m, 3H), 3.97 (t, J=3.8 Hz, 1H, 3'''''-H), 3.92 (t, J=8.8 Hz, 1H, 3-H), 3.90-3.73 (m, 11H), 3.73-3.63 (m, 7H), 3.63-3.55 (m, 2H), 3.55-3.48 (m, 3H), 3.46-3.42 (m, 2H), 3.40-3.27 (m, 3H, 5''''-H-5, 5'''''''-H, CH$_2$ in linker), 3.27 (dd, J=10.2, 3.5 Hz, 1H, 2''''''-H), 3.15-3.10 (m, 2H, 2'-H, 2'''''-H), 3.08-2.89 (m, 2H, CH$_2$ in linker), 1.70 (s, 3H, Ac), 1.59 (bs, 5H, Ac, CH$_2$ in linker), 1.46 (s, 3H, Ac), 1.38 (s, 3H, Ac), 1.49-1.25 (m, 4H, CH$_2$ in linker), 1.10 (s, 9H, tBu), 1.04 (s, 9H, tBu), 0.93 (s, 18H, tBu x 2); $^{13}$C NMR (150 MHz, CDCl$_3$): δ 170.11 (C), 170.09 (C), 170.0 (C), 169.4 (C), 165.54 (C), 165.46 (C), 165.0 (C), 164.8 (C), 156.6/156.0 (C), 137.94 (C), 137.90 (C), 137.8 (C), 137.6 (C), 137.40 (C), 137.36 (C), 137.19 (C), 137.15 (C), 137.1 (C), 136.9 (C), 136.8 (C), 136.0 (CH), 135.89 (CH), 135.86 (CH), 135.8 (CH), 135.62 (CH), 135.56 (CH), 135.52 (CH), 135.45 (C), 133.7 (C), 133.4 (CH), 133.34 (CH), 133.27 (C), 133.2 (C), 133.20 (C), 133.18 (C), 133.1 (CH), 133.0 (C), 132.9 (C), 132.8 (C), 132.2 (C), 131.4 (CH), 131.1 (CH), 131.04 (CH), 131.03 (CH), 130.2 (CH), 130.0 (CH), 129.83 (CH), 129.77 (CH), 129.7 (CH), 129.6 (CH), 129.5 (CH), 129.4 (CH), 129.15 (CH), 129.09 (CH), 129.01 (CH), 128.96 (C), 128.9 (CH), 128.8 (CH), 128.6 (CH), 128.54 (CH), 128.46 (CH), 128.4 (CH), 128.3 (CH), 128.2 (CH), 128.13 (CH), 128.10 (CH), 128.08 (CH), 127.9 (CH), 127.8 (CH), 127.72 (CH), 127.69 (CH), 127.65 (CH), 127.61 (CH), 127.59 (CH), 127.56 (CH), 127.5 (CH), 127.43 (CH), 127.38 (CH), 127.24 (CH), 127.18 (CH), 127.1 (CH), 126.4 (CH), 126.2 (CH), 126.0 (CH), 125.7 (CH), 125.3 (CH), 121.6 (C), 121.1 (C), 121.0 (C), 100.8 (CH), 99.8 (CH), 98.5 (CH), 98.3 (CH), 97.4 (CH), 97.3 (CH), 96.99 (CH), 96.96 (CH), 83.6 (CH), 83.3 (CH), 80.4 (CH), 78.4 (CH), 78.2 (CH), 78.0 (CH), 77.7 (CH), 76.0 (CH), 75.1 (CH$_2$), 74.7 (CH$_2$), 74.4 (CH), 74.3 (CH$_2$), 74.2 (CH$_2$), 74.0 (CH/CH$_3$), 73.9 (CH), 73.5 (CH), 73.4 (CH), 73.2 (CH), 73.1 (CH/CH$_2$), 72.94 (CH), 72.85 (CH), 72.83 (CH$_2$), 72.77 (CH), 72.6 (CH), 72.4 (CH), 72.2 (CH), 69.7/69.6 (CH$_2$), 69.1 (CH), 68.5 (CH), 67.1 (CH$_2$), 65.5 (CH), 64.8 (CH), 64.0 (CH), 63.5 (CH), 63.4 (CH), 63.1 (CH), 62.7 (CH$_2$), 62.4 (CH$_2$), 62.3 (CH$_2$), 62.0 (CH$_2$), 61.9 (CH$_2$), 61.4 (CH$_2$), 60.9 (CH$_2$), 50.4/50.1 (CH$_2$), 47.0/46.0 (CH$_2$), 29.0 (CH$_2$), 27.6/27.2 (CH$_2$), 26.93 (CH$_3$), 26.87 (CH$_3$), 26.81 (CH$_3$), 26.75 (CH$_3$), 26.7 (CH$_3$), 23.0 (CH$_2$), 21.4 (CH$_3$), 20.7 (CH$_3$), 20.34 (CH$_3$), 20.32 (CH$_3$), 19.9 (CH$_3$), 19.42 (C), 19.37 (C), 19.32 (C), 19.28 (C); HRMS (MALDI): m/z calcd for C$_{235}$H$_{249}$Br$_4$N$_{13}$O$_{47}$Si$_4$Na ([M+Na]$^+$): 4462.5806, found: 4462.5928.

N-Benzyl-N-benzyloxycarbonyl-5-aminopentyl [2-azido-3-O-(4-bromobenzyl)-6-O-tert-butyldiphenylsilyl-2-deoxy-4-O-(2-naphthyl methyl)-α-D-glucopyranosyl]-(1→4)-(3-O-benzyl-α-L-idopyranosyl)-(1→4)-[2-azido-3-O-(4-bromobenzyl)-6-O-tert-butyldiphenylsilyl-2-deoxy-α-D-glucopyranosyl]-(1→4)-(3-O-benzyl-β-D-glucopyranosyl)-(1→4)-[2-azido-3-O-(4-bromobenzyl)-6-O-tert-butyldiphenylsilyl-2-deoxy-α-D-glucopyranosyl]-(1→4)-(3-O-benzyl-α-L-idopyranosyl)-(1→4)-[2-azido-3-O-(4-bromobenzyl)-6-O-tert-butyldiphenylsilyl-2-deoxy-α-D-glucopyranosyl]-(1→4)-3-O-benzyl-β-D-glucopyranoside (14)

NaOMe (5 equiv. per acyl group) was added to a solution of the octasaccharide 13 (1.68 g, 0.38 mmol) in a mixed solvent (MeOH/CH$_2$Cl$_2$=1/1) at room temperature under N$_2$ atmosphere. After stirring for 16 h, the reaction was neutralized by adding DOWEX 50WX4-200 resin. The mixture was filtered, and the filtrate was concentrated under reduced pressure. The residue was purified by flash column chromatography to obtain the deacylated compound 14 (1.23 g, 85%). [α]$^{27}_D$+8.6 (c 5.0, CHCl$_3$); IR (thin film): ν 3476, 2929, 2109, 1684, 1254, 1070, 1030, 700 cm$^{-1}$; $^1$H NMR (600 MHz, CDCl$_3$): δ 7.83-7.80 (m, 1H, Ar—H), 7.78-7.711 (m, 2H, Ar—H), 7.71-7.68 (m, 4H, Ar—H), 7.68-7.65 (m, 2H, Ar—H), 7.61-7.59 (s, 1H, Ar—H), 7.49-7.47 (m, 2H, Ar—H), 7.45-7.33 (m, 39H, Ar—H), 7.33-7.27 (m, 13H, Ar—H), 7.27-7.25 (m, 3H, Ar—H), 7.23-7.18 (m, 5H, Ar—H), 7.12-7.16 (m, 7H, Ar—H), 7.04 (d, J=8.2 Hz, 2H, Ar—H), 7.00 (d, J=8.2 Hz, 2H, Ar—H), 5.64 (bs, 1H), 5.61 (d, J=3.8 Hz, 1H), 5.23 (s, 1H), 5.21-5.13 (m, 3H), 5.09 (d, J=10.7 Hz, 1H), 5.05 (d, J=3.7 Hz, 1H), 5.01 (d, J=4.1 Hz, 1H), 4.95-4.87 (m, 3H), 4.84-4.81 (m, 3H), 4.79-4.74 (m, 3H), 4.68-4.55 (m, 5H), 4.54-4.46 (m, 5H), 4.34-4.24 (m, 1H), 4.19-4.14 (m, 2H), 4.13-4.10 (m, 1H), 4.10-4.05 (m, 1H), 4.05-3.99 (m, 2H), 3.99-3.92 (m, 2H), 3.92-3.89 (m, 2H), 3.87-3.80 (m, 10H), 3.77-3.72 (m, 3H), 3.71-3.64 (m, 5H), 3.62-3.51 (m, 11H), 3.48-3.39 (m, 4H), 3.38-3.36 (m, 1H), 3.34-3.16 (m, 7H), 3.11-3.06 (m, 1H, CH$_2$ in linker), 3.05-2.99 (m, 1H, CH$_2$ in linker), 1.66-1.49 (m, 6H, CH$_2$ in linker), 1.10 (s, 9H, tBu), 1.08 (s, 9H, tBu), 1.05 (s, 9H, tBu), 1.04 (s, 9H, tBu); $^{13}$C NMR (150 MHz, CDCl$_3$): δ 156.7/156.3 (C), 138.4 (C), 137.7 (C), 137.5 (C), 137.4 (C), 136.8 (C), 136.7 (C), 136.6 (C), 136.00 (C), 135.97 (CH), 135.91 (CH), 135.87 (CH), 135.8 (CH), 135.7 (CH), 135.61 (CH), 135.57 (CH), 135.3 (C), 133.33 (C), 133.28 (C), 133.2 (C), 133.1 (C), 133.0 (C), 132.9 (C), 131.51 (CH), 131.47 (CH), 131.2 (CH), 129.9 (CH), 129.8 (CH), 129.71 (CH), 129.67 (CH), 129.6 (CH), 129.4 (CH), 129.3 (CH), 129.2 (CH), 128.52 (CH), 128.47 (CH), 128.4 (CH), 128.35 (CH), 128.31 (CH), 128.21 (CH), 128.18 (CH), 127.90 (CH), 127.85 (CH), 127.81 (CH), 127.76 (CH), 127.70 (CH), 127.68 (CH), 127.6 (CH), 127.5 (CH), 127.3 (CH), 127.2 (CH), 126.2 (CH), 126.1 (CH), 125.9 (CH), 125.5 (CH), 121.8 (C), 121.7 (C), 121.5 (C), 102.9/102.7 (CH), 102.1 (CH), 99.9 (CH), 99.8 (CH), 97.3 (CH), 97.1 (CH), 94.8 (CH), 94.2 (CH), 84.9 (CH), 84.6 (CH), 81.1 (CH), 79.4 (CH), 78.9 (CH), 78.6 (CH), 77.9 (CH), 77.2 (CH), 76.1 (CH), 75.8 (CH), 75.2 (CH), 75.1 (CH$_2$), 74.9 (CH$_2$), 74.74 (CH/CH$_2$), 74.66 (CH$_2$), 74.6 (CH), 74.3 (CH$_2$), 73.9 (CH$_2$), 73.0 (CH), 72.90 (CH), 72.85 (CH), 72.6 (CH), 72.4 (CH), 72.3 (CH/CH$_2$), 72.2 (CH$_2$), 72.0 (CH), 70.4 (CH), 70.0 (CH$_2$), 69.9 (CH), 67.2 (CH$_2$), 66.8 (CH), 66.7 (CH), 66.4 (CH), 66.2 (CH), 63.8 (CH), 63.6 (CH), 63.34 (CH), 63.31 (CH), 62.4 (CH$_2$), 62.3 (CH$_2$), 62.1 (CH$_2$), 62.0 (CH$_2$), 61.5 (CH$_2$), 61.31 (CH$_2$), 61.26 (CH$_2$), 53.7 (CH$_2$), 50.4/50.2

($CH_2$), 46.9/45.9 ($CH_2$), 29.6 ($CH_2$), 29.2 ($CH_2$), 28.8 ($CH_2$), 27.7 ($CH_2$), 26.88 ($CH_3$), 26.86 ($CH_3$), 26.84 ($CH_3$), 23.1 ($CH_2$), 19.42 (C), 19.38 (C), 19.31 (C); HRMS (MALDI): m/z calcd for $C_{199}H_{225}Br_4N_{13}O_{39}Si_4Na$ ([M+Na]$^+$): 3877.9968, found: 3877.9971.

N-Benzyl-N-benzyloxycarbonyl-5-aminopentyl [2-azido-3-O-(4-bromobenzyl)-6-O-tert-butyldiphenylsilyl-2-deoxy-4-O-(2-naphthyl methyl)-α-D-glucopyranosyl]-(1→4)-(methyl 3-O-benzyl-α-L-idopyranosyluronate)-(1→4)-[2-azido-3-O-(4-bromobenzyl)-6-O-tert-butyldiphenylsilyl-2-deoxy-α-D-glucopyranosyl]-(1→4)-(methyl 3-O-benzyl-β-D-glucopyranosyluronate)-(1→4)-[2-azido-3-O-(4-bromobenzyl)-6-O-tert-butyldiphenylsilyl-2-deoxy-α-D-glucopyranosyl]-(1→4)-(methyl 3-O-benzyl-α-L-idopyranosyluronate)-(1→4)-[2-azido-3-O-(4-bromobenzyl)-6-O-tert-butyldiphenylsilyl-2-deoxy-α-D-glucopyranosyl]-(1→4)-methyl 3-O-benzyl-β-D-glucopyranosiduronate (15)

Bis(acetoxy)iodobenzene (BAIB, 331 mg, 1.03 mmol) was added to a solution of the compound 14 (330 mg, 0.09 mmol) in a mixed solvent ($CH_2Cl_2$/$H_2O$=2/1, 3 mL) at room temperature. After 5 min, 2,2,6,6-tetramethyl-1-piperidinyloxyl free radical (TEMPO, 7 mg, 0.04 mmol) was placed into the mixture, which was, then, kept stirring for 8 h. To quench the reaction, 10% $Na_2S_2O_{3(aq)}$ (3 mL) was added, and the desired material was extracted with $CH_2Cl_2$. The combined organic layer was washed with brine, dried over anhydrous $MgSO_4$, filtered and concentrated under reduced pressure. To a solution of this residue in THF (2.5 mL) was then added LiOH (0.5 M solution in water, 1.7 mL, 0.9 mmol) at room temperature. After 4 h, the reaction was neutralized by adding DOWEX 50WX-200 resin, filtered and concentrated under reduced pressure. To the crude uronate solution in $CH_2Cl_2$ (3 mL) was added an ethereal solution of $CH_2N_2$ (3 mL, 1.28 mmol), and the reaction mixture was stirred at room temperature for 12 h. The reaction solution was quenched by acetic acid and the resulting mixture was concentrated under reduced pressure to yield the crude residue. Purification by flash column chromatography (ethyl acetate/hexane=1/5) gave compound 42 (220 mg, 65% overall). $[α]^{22}_D$+8.6 (c 4.0, $CHCl_3$); IR (thin film): ν 3514, 2931, 2110, 1754, 1215, 1112, 1013, 701 cm$^{-1}$; $^1$H NMR (600 MHz, $CDCl_3$): δ 7.88-7.80 (m, 1H, Ar—H), 7.75-7.66 (m, 16H, Ar—H), 7.65-7.62 (m, 2H, Ar—H), 7.59-7.57 (m, 1H, Ar—H), 7.50-7.44 (m, 5H, Ar—H), 7.40-7.31 (m, 38H, Ar—H), 7.31-7.23 (m, 23H, Ar—H), 7.18-7.14 (m, 1H, Ar—H), 7.14-7.11 (m, 2H, Ar—H), 7.10-7.06 (m, 2H, Ar—H), 7.05-7.02 (m, 2H, Ar—H), 5.54-5.49 (m, 2H), 5.38 (s, 2H), 5.20-5.14 (m, 2H), 5.05-4.99 (m, 2H), 4.99-4.91 (m, 3H), 4.90-4.85 (m, 1H), 4.82-4.73 (m, 6H), 4.69-4.62 (m, 3H), 4.61-4.53 (m, 4H), 4.51-4.45 (m, 5H), 4.30-4.21 (m, 1H), 4.16-4.09 (m, 2H), 4.09-4.03 (m, 2H), 4.01-3.92 (m, 5H), 3.91-3.84 (m, 7H), 3.83-3.77 (m, 6H), 3.75-3.71 (m, 3H), 3.70-3.65 (m, 3H), 3.63-3.57 (m, 1H), 3.56-3.50 (m, 2H), 3.50-3.45 (m, 3H), 3.42-3.30 (m, 9H), 3.27-3.22 (m, 6H), 3.19-3.13 (m, 5H), 1.74-1.45 (m, 6H), 1.10 (s, 9H, tBu), 1.073 (s, 9H, tBu), 1.070 (s, 9H, tBu), 1.06 (s, 9H, tBu); $^{13}$C NMR (150 MHz, $CDCl_3$): δ 169.0 (C), 168.6 (C), 168.1 (C), 156.7/156.3 (C), 138.3 (C), 138.23 (C), 138.16 (C), 137.8 (C), 137.14 (C), 137.12 (C), 137.0 (C), 136.92 (C), 136.86 (C), 136.8 (C), 136.7 (C), 136.60 (C), 136.57 (C), 136.0 (CH), 135.9 (CH), 135.82 (CH), 135.79 (CH), 135.6 (CH), 135.54 (CH), 135.49 (CH), 133.5 (C), 133.4 (C), 133.3 (C), 133.21 (C), 133.18 (C), 133.10 (C), 133.08 (C), 133.0 (C), 132.93 (C), 132.90 (C), 132.87 (C), 132.75 (C), 131.5 (CH), 131.4 (CH), 131.11 (CH), 131.08 (CH), 130.4 (CH), 130.0 (CH), 129.9 (CH), 129.74 (CH), 129.72 (CH), 129.68 (CH), 129.65 (CH), 129.63 (CH), 129.60 (CH), 129.1 (CH), 129.0 (CH), 128.61 (CH), 128.58 (C), 128.5 (CH), 128.4 (CH), 128.34 (CH), 128.29 (CH), 128.21 (CH), 128.17 (CH), 128. (CH), 128.0 (CH), 127.9 (CH), 127.84 (CH), 127.81 (CH), 127.71 (CH), 127.66 (CH), 127.55 (CH), 127.53 (CH), 127.32 (CH), 127.28 (CH), 127.17 (CH), 126.2 (CH), 125.9 (CH), 125.8 (CH), 125.2 (CH), 121.8 (C), 121.7 (C), 121.08 (C), 121.06 (C), 103.1 (CH), 102.8 (CH), 102.2 (CH), 101.0 (CH), 100.8 (CH), 97.20 (CH), 97.15 (CH), 95.4 (CH), 95.2 (CH), 84.2 (CH), 84.0 (CH), 80.9 (CH), 79.2 (CH), 78.3 (CH), 78.1 (CH), 77.6 (CH), 76.1 (CH), 75.1 ($CH_2$), 74.92 ($CH_2$), 74.89 ($CH_3$), 74.87 ($CH_2$), 74.8 (CH), 74.7 ($CH_2$), 74.6 (CH), 74.5 ($CH_2$), 74.4 ($CH_2$), 74.2 (CH), 74.0 (CH), 73.7 (CH), 73.6 (CH), 73.1 ($CH_2$), 72.9 ($CH_2$), 72.7 (CH), 72.55 (CH), 72.49 ($CH_2$), 72.4 (CH/$CH_2$), 72.3 (CH), 72.2 ($CH_2$), 72.1 (CH), 72.0 (CH), 71.4 (CH), 70.4/70.0 ($CH_2$), 67.4 (CH), 67.2 ($CH_2$), 67.1 (CH), 66.9 (CH), 66.6 (CH), 63.7 (CH), 63.2 (CH), 63.0 (CH), 62.1 ($CH_2$), 61.9 ($CH_2$), 61.1 ($CH_2$), 53.8 ($CH_2$), 52.3 ($CH_3$), 52.1 ($CH_3$), 51.7 ($CH_3$), 51.6 ($CH_3$), 50.4/50.2 ($CH_2$), 46.9/45.9 ($CH_2$), 31.9 ($CH_2$), 29.7 ($CH_2$), 29.6 ($CH_2$), 29.3 ($CH_2$), 26.92 ($CH_3$), 29.0/28.8 ($CH_2$), 27.0 ($CH_3$), 26.94 ($CH_3$), 26.89 ($CH_3$), 23.3 ($CH_2$), 23.0 ($CH_2$), 22.70 ($CH_2$), 22.67 ($CH_2$), 22.6 ($CH_2$), 19.42 (C), 19.41 (C), 19.37 (C); HRMS (MALDI): m/z calcd for $C_{203}H_{225}Br_4N_{13}O_{43}Si_4Na$ ([M+Na]$^+$): 3990.0383, found: 3990.0508.

N-Benzyl-N-benzyloxycarbonyl-5-aminopentyl [2-azido-3-O-(4-bromobenzyl)-2-deoxy-4-O-(2-naphthylmethyl)-α-D-glucopyranosyl]-(1→4)-(methyl 3-O-benzyl-α-L-idopyranosyluronate)-(1→4)-[2-azido-3-O-(4-bromobenzyl)-2-deoxy-α-D-glucopyranosyl]-(1→4)-(methyl 3-O-benzyl-β-D-glucopyranosyluronate)-(1→4)-[2-azido-3-O-(4-bromobenzyl)-2-deoxy-α-D-glucopyranosyl]-(1→4)-(methyl 3-O-benzyl-α-L-idopyranosyluronate)-(1→4)-[2-azido-3-O-(4-bromobenzyl)-2-deoxy-α-D-glucopyranosyl]-(1→4)-methyl 3-O-benzyl-β-D-glucopyranosiduronate (16)

A 70% solution of HF in pyridine (500 equiv.) was added to an ice-cooled solution of the compound 15 (210 mg, 0.05 mmol) in a mixed solvent (pyridine/THF=1/1, v/v, 40 mL/g of octasaccharide). The mixture was allowed to warm to room temperature and stirred for 3 d. The solution was concentrated under reduced pressure, and the residue was purified by flash column chromatography to afford the compound 16 (135 mg, 83%). $[α]^{27}_D$ −29.7 (c 2.0, $CHCl_3$); IR (thin film): ν 2924, 2109, 1748, 1027, 699 cm$^{-1}$; $^1$H NMR (600 MHz, $CDCl_3$): δ 7.81-7.79 (m, 1H, Ar—H), 7.78-7.74 (m, 2H, Ar—H), 7.63 (bs, 1H, Ar—H), 7.48-7.45 (m, 2H, Ar—H), 7.43-7.41 (m, 2H, Ar—H), 7.38-7.34 (m, 18H, Ar—H), 7.33-7.30 (m, 8H, Ar—H), 7.30-7.26 (m, 7H, Ar—H), 7.25-7.22 (m, 4H, Ar—H), 7.20-7.18 (m, 2H, Ar—H), 7.16-7.13 (m, 1H, Ar—H), 7.10-7.07 (m, 2H, Ar—H), 7.04-7.00 (m, 4H, Ar—H), 5.56 (bs, 1H), 5.47 (d, J=3.5 Hz, 1H), 5.23 (d, J=8.5 Hz, 2H), 5.19-5.12 (m, 2H), 5.11-5.03 (m, 1H), 4.99-4.95 (m, 2H), 4.92 (d, J=10.9 Hz, 1H), 4.89 (d, J=3.5 Hz, 1H), 4.86 (d, J=11.8 Hz, 1H), 4.81-4.77 (m, 3H), 4.74-4.72 (m, 3H), 4.71 (d, J=5.0 Hz, 1H), 4.69 (d, J=5.0 Hz, 1H), 4.61-4.56 (m, 3H), 4.56-4.50 (m, 3H), 4.49-4.42 (m, 4H), 4.31-4.24 (m, 1H), 4.07 (t, J=9.0

Hz, 1H), 4.03 (t, J=9.0 Hz, 1H), 4.00 (bs, 1H), 3.98-3.93 (m, 3H), 3.92-3.85 (m, 4H), 3.85-3.81 (m, 3H), 3.81-3.78 (m, 2H), 3.78-3.75 (m, 3H), 3.73-3.69 (m, 8H), 3.68-3.65 (m, 3H), 3.65-3.62 (m, 3H), 3.62-3.59 (m, 3H), 3.58-3.55 (m, 2H), 3.51 (s, 3H), 3.50-3.49 (m, 1H), 3.49-3.46 (m, 1H), 3.45-3.43 (m, 5H), 3.42-3.41 (m, 1H), 3.40-3.37 (m, 4H), 3.24-3.18 (m, 3H), 1.34-1.25 (m, 6H, $CH_2$ in linker); $^{13}C$ NMR (150 MHz, $CDCl_3$): δ 169.5 (C), 169.4 (C), 168.8 (C), 168.5 (C), 156.7/156.3 (C), 138.12 (C), 138.06 (C), 138.0 (C), 137.7 (C), 137.0 (C), 136.8 (C), 136.72 (C), 136.65 (C), 136.52 (C), 136.47 (C), 135.0 (C), 133.1 (C), 132.9 (C), 131.45 (CH), 131.37 (CH), 131.14 (CH), 131.10 (CH), 129.52 (CH), 129.46 (CH), 129.0 (CH), 128.9 (CH), 128.6 (CH), 128.5 (CH), 128.40 (CH), 128.36 (CH), 128.3 (CH), 127.9 (CH), 127.8 (CH), 127.7 (CH), 127.6 (CH), 127.2 (CH), 127.1 (CH), 126.28 (CH), 126.27 (CH), 126.1 (CH), 125.4 (CH), 121.7 (C), 121.5 (C), 121.14 (C), 121.09 (C), 103.2 (CH), 103.1 (CH), 102.9 (CH), 100.9 (CH), 100.7 (CH), 97.4 (CH), 97.2 (CH), 96.0 (CH), 95.4 (CH), 83.9 (CH), 80.7 (CH), 79.3 (CH), 78.4 (CH), 78.3 (CH), 76.2 (CH), 75.0 ($CH_2$), 74.9 ($CH_2$), 74.8 ($CH_2$), 74.73 ($CH_2$), 74.66 (CH), 74.6 ($CH_3$), 74.5 (CH), 74.1 (CH), 73.9 (CH), 73.50 ($CH_2$), 73.47 ($CH_2$), 73.1 (CH), 72.9 (CH), 72.6 ($CH_2$), 72.5 ($CH_2$), 72.2 ($CH_2$), 72.1 (CH), 71.9 (CH), 71.6 ($CH_2$), 71.0 ($CH_2$), 70.4 ($CH_2$), 70.3 ($CH_2$), 70.0 ($CH_2$), 67.7 (CH), 67.5 (CH), 67.2 ($CH_3/CH_2$), 67.1 (CH), 66.8 (CH), 63.5 (CH), 63.4 (CH), 63.3 (CH), 61.8 ($CH_2$), 61.0 ($CH_2$), 60.9 ($CH_2$), 60.3 ($CH_2$), 52.7 ($CH_3$), 52.6 ($CH_3$), 52.14 ($CH_3$), 52.13 ($CH_3$), 50.4/50.2 ($CH_2$), 46.9/45.9 ($CH_2$), 31.9 ($CH_2$), 31.6 ($CH_2$), 30.0 ($CH_3$), 29.63 ($CH_2$), 29.59 ($CH_2$), 29.3 ($CH_2$), 29.0 ($CH_2$), 28.7 ($CH_2$), 27.6 ($CH_2$), 27.1 ($CH_2$), 27.0 ($CH_2$), 23.2 ($CH_2$), 23.0 ($CH_2$), 22.6 ($CH_2$), 19.2 (C), 14.1 ($CH_2$), 13.9 (C); HRMS (MALDI): m/z calcd for $C_{139}H_{153}Br_4N_{13}O_{43}Na$ $[M+Na]^+$: 3036.4155, found: 3036.4241.

N-Benzyl-N-benzyloxycarbonyl-5-aminopentyl [2-azido-3-O-(4-bromobenzyl)-2-deoxy-4-O-(2-naphthylmethyl)-6-O-sulfonato-α-D-glucopyranosyl)-(1→4)-(methyl 3-O-benzyl-2-O-sulfonato-α-L-idopyranosyluronate)-(1→4)-[2-azido-3-O-(4-bromobenzyl)-2-deoxy-6-O-sulfonato-α-D-glucopyranosyl]-(1→4)-(methyl 3-O-benzyl-2-O-sulfonato-β-D-glucopyranosyluronate)-(1→4)-[2-azido-3-O-(4-bromobenzyl)-2-deoxy-6-O-sulfonato-α-D-glucopyranosyl]-(1→4)-(methyl 3-O-benzyl-2-O-sulfonato-α-L-idopyranosyluronate)-(1→4)-[2-azido-3-O-(4-bromo benzyl)-2-deoxy-6-O-sulfonato-α-D-glucopyranosyl]-(1→4)-methyl 3-O-benzyl-2-O-sulfonato-β-D-glucopyranosiduronate octasodium Salt (17)

A solution of compound 16 (190 mg, 0.06 mmol) and $SO_3.Et_3N$ (4 equiv. per OH group of the octasaccharide) in DMF (10 mL/g of octasaccharide) was kept stirring at 60° C. under $N_2$ for 1 d. The reaction flask was cooled down to room temperature, a solution of phosphate buffer (pH=7, 2.0 mL) was added and the mixture was kept stirring for another 30 min. The resulting solution was concentrated in vacuo, and the residue was purified by Sephadex LH-20 with MeOH as eluent to get the O-sulfonated compound 17 (226 mg, 94%). IR (thin film): ν 3464, 2111, 1747, 1236, 1068, 1005, 701 $cm^{-1}$; $^1H$ NMR (600 MHz, $CD_3OD$): δ 7.81-7.72 (m, 3H, Ar—H), 7.70 (bs, 1H, Ar—H), 7.55-7.49 (m, 6H, Ar—H), 7.46-7.37 (m, 18H, Ar—H), 7.36-7.33 (m, 5H, Ar—H), 7.32-7.26 (m, 9H, Ar—H), 7.25-7.21 (m, 4H, Ar—H), 7.21-7.17 (m, 3H, Ar—H), 7.04 (d, J=8.5 Hz, 2H, Ar—H), 7.01 (d, J=8.4 Hz, 2H, Ar—H), 5.56 (s, 1H), 5.48-5.42 (m, 3H), 5.32 (d, J=10.0 Hz, 1H), 5.19-5.09 (m, 5H), 5.04 (d, J=3.0 Hz, 1H), 4.99-4.94 (m, 2H), 4.93-4.91 (m, 1H), 4.85-4.77 (m, 8H, Ar$CH_2$), 4.73-4.70 (m, 2H), 4.69-4.68 (m, 1H), 4.67-4.63 (m, 2H), 4.59 (s, 2H), 4.55-4.48 (m, 4H), 4.45-4.38 (m, 3H), 4.37-4.31 (m, 4H), 4.30-4.25 (m, 3H), 4.25-4.20 (m, 5H), 4.15-4.10 (m, 2H), 4.06 (t, J=9.5 Hz, 1H), 4.04-3.99 (m, 2H), 3.97 (dd, J=8.5, 4.9 Hz, 1H), 3.91-3.86 (m, 4H), 3.86-3.83 (m, 1H), 3.80 (s, 3H), 3.76-3.71 (m, 2H), 3.71-3.64 (m, 6H), 3.64-3.59 (m, 3H), 3.55 (s, 3H), 3.48-3.46 (m, 1H), 3.45 (s, 3H), 3.43-3.41 (m, 1H), 3.41-3.38 (m, 1H), 3.30-3.27 (m, 2H), 3.26-3.18 (m, 2H), 1.64-1.50 (m, 4H, $CH_2$ in linker), 1.41-1.29 (m, 2H, $CH_2$ in linker); $^{13}C$ NMR (150 MHz, $CD_3OD$): δ 172.6 (C), 172.2 (C), 171.8 (C), 170.9 (C), 158.6/158.1 (C), 139.8 (C), 139.6 (C), 139.5 (C), 139.4 (C), 139.1 (C), 138.83 (C), 138.81 (C), 138.3 (C), 138.2 (C), 137.2 (C), 134.8 (C), 134.5 (C), 132.40 (CH), 132.37 (CH), 132.36 (CH), 132.2 (CH), 131.6 (CH), 130.7 (CH), 130.52 (CH), 130.46 (CH), 130.4 (CH), 129.3 (CH), 129.8 (CH), 129.73 (CH), 129.66 (CH), 129.6 (CH), 129.5 (CH), 129.29 (CH), 129.25 (CH), 129.11 (CH), 129.05 (CH), 129.0 (CH), 128.8 (CH), 128.7 (CH), 128.5 (CH), 128.4 (CH), 127.7 (CH), 127.2 (CH), 127.1 (CH), 126.9 (CH), 122.33 (C), 122.26 (C), 122.2 (C), 122.1 (C), 102.7 (CH), 101.8 (CH), 99.6 (C), 98.8 (CH), 98.6 (CH), 98.5 (CH), 98.4 (CH), 98.2 (CH), 84.1 (CH), 83.8 (CH), 81.7 (CH), 80.4 (CH), 80.3 (CH), 80.2 (CH), 80.0 (CH), 79.6 (CH), 78.9 (CH), 78.8 (CH), 77.0 (CH), 76.1 ($CH_2$), 75.65 ($CH_2$), 75.6 ($CH_2$), 75.4 ($CH_2/CH$), 75.2 (CH), 75.0 (CH), 74.9 ($CH_2$), 74.8 ($CH_2$), 74.2 ($CH_2$), 73.6 ($CH_2$), 73.5 ($CH_2$), 73.4 (CH), 73.2 (CH), 72.5 (CH), 72.2 (C), 72.0 (C), 71.9 (C), 71.8 (CH), 71.5 (CH), 70.5 (CH), 70.32 (CH), 70.26 ($CH_2$), 70.1 ($CH_2$), 68.6 ($CH_2$), 68.4 ($CH_2$), 68.1 (CH), 68.0 (CH), 67.3 ($CH_2$), 67.03 ($CH_2$), 66.98 ($CH_2$), 66.6 ($CH_2$), 65.4 (CH), 65.0 (CH), 54.1 (CH), 53.6 (CH), 51.6 ($CH_2$), 51.5 ($CH_2$), 47.7 ($CH_2$), 30.1 ($CH_2$), 30.0 ($CH_2$), 29.0 ($CH_2$), 28.6 ($CH_2$), 24.32 ($CH_2$), 24.25 ($CH_2$); LRMS (ESI): m/z calcd for $C_{139}H_{145}Br_4N_{13}Na_{10}O_{67}S_8$ $([M-8H+10Na]^{2+})$: 1937.9, found: 1937.6.

O-sulfonato-α-D-glucopyranosyl]-(1→4)-(3-O-benzyl-2-O-sulfonato-β-D-glucuronopyranosyl)-(1→4)-[2-azido-3-O-(4-bromobenzyl)-2-deoxy-6-O-sulfonato-α-D-glucopyranosyl]-(1→4)-(3-O-benzyl-2-O-sulfonato-α-L-iduronopyranosyl)-(1→4)-[2-azido-3-O-(4-bromo-benzyl)-2-deoxy-6-O-sulfonato-α-D-glucopyranosyl]-(1→4)-3-O-benzyl-2-O-sulfonato-β-D-glucuronopyranoside dodecasodium Salt (18)

$CHCl_3$ (2.4 ml), MeOH (8.8 ml), NaOH (5 M solution in $H_2O$, 1.2 mL) and $H_2O$ (1.2 mL) were added to the compound 17 (155 mg, 0.05 mmol) at room temperature. The mixture was kept stirring for 2 d, and the reaction solution was neutralized by 1 N $HCl_{(aq)}$. The mixture was concentrated in vacuo, and the residue was purified by gel permeation chromatography on Sephadex LH-20 using MeOH as eluent. The appropriate fractions were pooled and passed through a column of AG 50W-X8 $Na^+$ resin with MeOH to get compound 18 (150 mg, 96%).

$^1H$ NMR (600 MHz, $CD_3OD$): δ 7.81-7.72 (m, 4H, Ar—H), 7.50-7.47 (m, 4H, Ar—H), 7.46-7.42 (m, 7H, Ar—H), 7.40-7.37 (m, 5H, Ar—H), 7.36-7.32 (m, 5H, Ar—H), 7.30-7.27 (m, 10H, Ar—H), 7.27-7.24 (m, 7H, Ar—H), 7.24-7.21 (m, 5H, Ar—H), 7.21-7.19 (m, 3H, Ar—H), 7.19-7.16 (m, 3H, Ar—H), 5.64 (s, 1H), 5.59 (s, 1H), 5.52 (d, J=3.1 Hz, 1H), 5.49 (d, J=2.8 Hz, 1H), 5.30-5.24 (m, 3H), 5.19-5.09 (m, 4H), 5.05-4.96 (m, 5H), 4.89-4.86 (m, 2H), 4.81-4.78 (m, 2H), 4.68-4.62 (m, 6H, ArCH$_2$), 4.60-4.54 (m, 7H), 4.53-4.49 (m, 4H), 4.41-4.36 (m, 4H), 4.33-4.27 (m, 3H), 4.25-4.18 (m, 6H), 4.16-4.12 (m, 3H), 4.10-4.04 (m, 3H), 4.03-3.98 (m, 3H), 3.97-3.93 (m, 3H), 3.92-3.89 (m, 2H), 3.88-3.83 (m, 3H), 3.69 (t, J=9.4 Hz, 1H), 3.60-3.49 (m, 2H), 3.40-3.36 (m, 1H), 3.29-3.18 (m, 3H), 3.13 (d, J=9.1 Hz, 1H), 1.60-1.47 (m, 4H, CH$_2$ in linker), 1.40-1.28 (m, 2H, CH$_2$ in linker); $^{13}$C NMR (150 MHz, CD$_3$OD): δ 176.4 (C), 176.1 (C), 175.9 (C), 158.6/158.0 (C), 140.0 (C), 139.9 (C), 139.5 (C), 139.4 (C), 139.3 (C), 139.2 (C), 139.14 (C), 139.06 (C), 139.0 (C), 138.2 (C), 138.1 (C), 137.2 (C), 134.8 (C), 134.5 (C), 132.4 (CH), 132.3 (CH), 132.2 (CH), 131.7 (CH), 131.0 (CH), 130.4 (CH), 129.8 (CH), 129.72 (CH), 129.67 (CH), 129.6 (CH), 129.5 (CH), 129.44 (CH), 129.39 (CH), 129.3 (CH), 129.23 (CH), 129.17 (CH), 129.1 (CH), 129.04 (CH), 128.99 (CH), 128.92 (CH), 128.86 (CH), 128.8 (CH), 128.7 (CH), 128.5 (CH), 128.4 (CH), 128.3 (CH), 128.1 (CH), 127.6 (CH), 127.1 (CH), 126.9 (CH), 122.2 (C), 122.09 (C), 122.07 (C), 102.8 (CH), 102.0 (CH), 98.3 (C), 98.0 (CH), 97.1 (CH), 96.9 (CH), 96.5 (CH), 85.2 (CH), 85.0 (CH), 82.0 (CH), 81.8 (CH), 81.4 (CH), 80.3 (CH), 79.3 (CH), 78.9 (CH), 78.6 (CH), 78.5 (CH), 78.3 (CH), 78.1 (CH), 76.9 (CH), 76.1 (CH$_2$), 75.9 (CH), 75.5 (CH$_2$), 75.3 (CH$_2$), 73.2 (CH$_2$/CH), 73.0 (CH$_2$/CH), 72.6 (CH), 72.4 (CH), 71.65 (CH), 71.56 (CH), 71.2 (CH$_2$), 71.0 (CH), 70.1 (CH), 69.31 (CH), 69.27 (CH), 68.9 (CH$_2$), 68.5 (CH$_2$), 68.4 (CH$_2$), 67.5 (CH$_2$), 65.7 (CH), 65.5 (CH), 65.2 (CH), 65.1 (CH), 51.7 (CH$_2$), 51.4 (CH$_2$), 50.0 (CH$_2$), 47.8 (CH$_2$), 30.2 (CH$_2$), 29.2 (CH$_2$), 28.6 (CH$_2$), 24.2 (CH$_2$); HRMS (MALDI): m/z calcd for C$_{135}$H$_{133}$Br$_4$N$_{13}$O$_{67}$S$_8$Na$_{14}$ ([M+14Na−12H]$^{2+}$): 1953.7903, found: 1953.7806.

(2R,3S,4S,5R,6R)-3-(((2R,3R,4R,5S,6R)-3-amino-4,5-dihydroxy-6-((sulfonatooxy)methyl)tetrahydro-2H-pyran-2-yl)oxy)-6-(((2R,3S,4R,5R,6R)-5-amino-6-(((2S,3S,4S,5R,6R)-6-(((2R,3S,4R,5R,6R)-5-amino-6-(((2R,3S,4S,5R,6R)-6-(((2R,3S,4R,5R,6R)-5-amino-6-(((2S,3S,4S,5R,6R)-6-((5-aminopentyl)oxy)-2-carboxylato-4-hydroxy-5-(sulfonatooxy)tetrahydro-2H-pyran-3-yl)oxy)-4-hydroxy-2-((sulfonatooxy)methyl)tetrahydro-2H-pyran-3-yl)oxy)-2-carboxylato-4-hydroxy-5-(sulfonatooxy)tetrahydro-2H-pyran-3-yl)oxy)-4-hydroxy-2-((sulfonatooxy)methyl)tetrahydro-2H-pyran-3-yl)oxy)-2-carboxylato-4-hydroxy-5-(sulfonatooxy)tetrahydro-2H-pyran-3-yl)oxy)-4-hydroxy-2-((sulfonatooxy)methyl)tetrahydro-2H-pyran-3-yl)oxy)-4-hydroxy-5-(sulfonatooxy)tetrahydro-2H-pyran-2-carboxylate (19)

A solution of the compound 18 and Pd(OH)$_2$ on carbon (3 g/g of the octasaccharide) in phosphate buffer (pH=7.0, 15 mL/g of the octasaccharide) with added MeOH as necessary to improve solubility of the octasaccharide was equipped with a hydrogen balloon and the mixture was stirred at room temperature for 2 d. The whole mixture was filtered through Celite and the filtrate was concentrated in vacuo. The residue was purified through a Sephadex G-25 column with H$_2$O as eluent followed by Na$^+$ exchange through AG 50WX8 (Na$^+$ form) cation exchange resin. Lyophilization of the appropriate fractions afforded the desired product 19 (80%).

$^1$H NMR (600 MHz, D$_2$O) δ 5.52 (d, J=3.8 Hz, 1H), 5.46 (d, J=3.7 Hz, 1H), 5.31 (t, J=4.4 Hz, 1H), 5.16 (d, J=4.1 Hz, 1H), 4.84 (d, J=1.8 Hz, 1H), 4.80 (brs, 1H), 4.52 (d, J=7.8 Hz, 1H), 4.47 (d, J=11.0 Hz, 1H), 4.29-4.25 (m, 4H), 4.19-4.07 (m, 7H), 4.01 (dd, J=8.8, 7.9 Hz, 1H), 3.97-3.91 (m, 2H), 3.90-3.70 (m, 14H), 3.64 (t, J=9.8 Hz, 1H), 3.62-3.59 (m, 1H), 3.47 (t, J=9.7 Hz, 1H), 3.28 (dd, J=10.7, 3.8 Hz, 1H), 3.23-3.16 (m, 2H), 2.91 (t, J=7.3 Hz, 2H), 1.63-1.53 (m, 4H), 1.44-1.36 (m, 2H); $^{13}$C NMR (150 MHz, D$_2$O) δ 175.3, 175.0, 174.6, 174.6, 100.5, 100.0, 98.8, 98.5, 96.4, 96.0, 91.7, 91.4, 80.0, 79.6, 77.1, 76.9, 76.1, 76.0, 75.8, 75.1, 75.0, 74.9, 72.9, 72.7, 70.8, 70.4, 70.2, 70.1, 69.7, 69.5, 69.3, 68.9, 68.6, 68.4, 67.7, 67.2, 67.1, 66.1, 66.0, 65.4, 63.1, 62.8, 54.3, 54.1, 53.9, 39.4, 27.9, 26.1, 21.8; HRMS (ESI): m/z calcd for C$_{53}$H$_{87}$N$_5$Na$_4$O$_{65}$S$_8$ ([M+10H-8Na]$^{2+}$): 1090.5501, found: 1090.5498.

Compound 20:

To the octasaccharide amine compound 19 in 10% water in DMF (220 μL/1 mg), Et$_3$N (25 μL/1 mg) and freshly prepared activated biotin ester (75 μL/1 mg of 0.1M in DMF, 15 eq) were added at rt. Stirring was continued for another 16 h at rt. Evaporated the solvent using N$_2$ gas stream and purified using G-10 sephadex size exclusive column chromatography followed by Na$^+$ exchange by passing through AG 50WX8 (Na$^+$ form) cation exchange resin column. Lyophilization of the appropriate fractions afforded the desired compound 20 as a white foam solid in 94%.

$^1$H NMR (600 MHz, D$_2$O) δ 5.37-5.26 (m, 1H), 5.10 (s, 1H), 5.08-5.04 (m, 1H), 4.62-4.60 (m, 1H), 4.54-4.50 (m, 3H), 4.50-4.41 (m, 2H), 4.35-4.32 (m, 3H), 4.30-4.20 (m, 4H), 4.13 (brs, 3H), 4.06-4.00 (m, 1H), 3.97 (brs, 2H), 3.93-3.88 (m, 4H), 3.83-3.76 (m, 2H), 3.76-3.63 (m, 21H), 3.70-3.53 (m, 120H), 3.59-3.51 (m, 20H), 3.52-3.43 (m, 1H), 3.31-3.29 (m, 10H), 3.26-3.23 (m, 6H), 3.09 (t, J=6.8 Hz, 1H), 3.02 (d, J=13.3 Hz, 1H), 2.95-2.85 (m, 4H), 2.83 (dd, J=13.3, 4.7 Hz, 1H), 2.70 (s, 2H), 2.68 (s, 1H), 2.62-2.54 (m, 2H), 2.52-2.50 (m, 2H), 2.42 (t, J=6.2 Hz, 1H), 2.38-2.36 (m, 4H), 2.20-2.17 (m, 10H), 1.68-1.40 (m, 21H), 1.34-1.31 (m, 10H); $^{13}$C NMR (150 MHz, D$_2$O) δ 180.2, 180.1, 176.9, 176.9, 175.2, 174.6, 174.4, 174.2, 174.0, 173.7, 165.3, 165.3, 163.1, 160.2, 100.4, 99.9, 99.1, 98.9, 97.1, 96.9, 94.4, 94.0, 80.3, 79.9, 76.5, 76.2, 75.5, 74.2, 71.6, 71.0, 70.4, 69.6, 69.6, 69.5, 69.5, 69.4, 69.4, 69.3, 69.3, 68.8, 67.9, 66.8, 66.7, 66.7, 66.5, 66.4, 66.2, 65.0, 64.4, 62.1, 60.2, 59.5, 59.5, 58.4, 55.3, 55.3, 55.1, 53.6, 53.2, 52.9, 50.2, 40.9, 39.7, 39.7, 39.4, 38.9, 38.9, 37.6, 37.1, 36.1, 35.9, 35.8, 35.7, 35.6, 35.4, 35.4, 28.5, 28.3, 27.9, 27.8, 27.7, 27.7, 27.6, 25.1, 25.1, 22.4; HRMS (ESI): m/z calcd for C$_{178}$H$_{299}$N$_{20}$O$_{110}$S$_{13}$ ([M+7H−12Na]$^{5-}$): 979.0973, found: 979.0985.

Example 2 CTC Detection by Use of Magnetic Beads Pre-Coated with the Compound of Example 1

A microfluid chip for capturing CTCs from 65 advanced or metastatic CCA samples was constructed, and CTCs in all 65 bold samples were respectively captured using magnetic beads pre-coated with the compound of Example 1 (i.e., MB-SCH45) or an EpCAM antibody (i.e., MB-anti-EpCAM, as a control) in accordance with the procedures described in the "Materials and Methods" section.

It was found that MB-SCH45 was capable of isolating CTCs from all samples, regardless of the disease status. The number of CTCs isolated from the above samples using MB-SCH45 and MB-anti-EpCAM and details regarding the stage and organ of metastasis have been presented in Table 1. It is noteworthy that CTCs could be detected even in the blood of patients (Nos. 5, 14, 23, 30, 32, 43, and 60 in Table 1) with no distant metastasis as observed by radiographic imaging at the time of observation. We also observed that the size of the CTCs ranged from 5 to 20 μm in diameter (data not shown). Most of the cells presented a high nucleus-to-cytoplasmic ratio but not in all cases. We also documented dramatic heterogeneity in terms of cell shapes among patients as has been documented in other studies. Experimental data revealed that MB-SCH45 and MB-anti-EpCAM led to the isolation of ≥1 and ≥3 CTCs mL of blood respectively. Furthermore, several stage-V patients being characterized by the lowest concentrations and nonmetastatic patients displaying significant number of CTCs was also observed.

TABLE 1

Number of CTCs isolated/mL of blood. Information of the disease, organ of metastasis, stage and number of CTCs isolated using MB-SCH45 or MB-anti-EpCAM

| | | | | No. of CTC isolated | |
|---|---|---|---|---|---|
| Sample # | Disease | Organ of metastasis | Stage | MB-SCH45 | MB-anti-EpCAM |
| 1 | Intrahepatic cholangiocarcinoma | Distant lymph nodes | IV | 12 | 28 |
| 2 | Intrahepatic cholangiocarcinoma | Peritoneal seeding | IV | 3 | 10 |
| 3 | Hilar cholangiocarcinoma | Neck lymph nodes | IV | 4 | 20 |
| 4 | Intrahepatic cholangiocarcinoma | lymph nodes metastasis and peritoneal seeding | IV | 45 | 122 |
| 5 | Intrahepatic cholangiocarcinoma | No distant metastasis | III | 24 | 90 |
| 6 | Intrahepatic cholangiocarcinoma | Lymph nodes | III | 30 | 98 |
| 7 | Intrahepatic cholangiocarcinoma | Peritoneal seeding | IV | 3 | 10 |
| 8 | Intrahepatic cholangiocarcinoma | Brain metastasis | IV | 6 | 15 |
| 9 | Hilar cholangiocarcinoma | Neck lymph nodes | IV | 6 | 20 |
| 10 | Intrahepatic cholangiocarcinoma | Liver metastasis | IV | 38 | 126 |
| 11 | Intrahepatic cholangiocarcinoma | lymph nodes metastasis and peritoneal seeding | IV | 50 | 121 |
| 12 | Intrahepatic cholangiocarcinoma | Lymph nodes | IV | 15 | 45 |
| 13 | Intrahepatic cholangiocarcinoma | Lymph nodes | III | 4 | 15 |
| 14 | Intrahepatic cholangiocarcinoma | No distant metastasis | III | 12 | 15 |
| 15 | Intrahepatic cholangiocarcinoma | Lymph nodes | III | 60 | 120 |
| 16 | Hilar cholangiocarcinoma | Adrenal gland | IV | 70 | 104 |
| 17 | Intrahepatic cholangiocarcinoma | Peritoneal seeding | IV | 47 | 102 |
| 18 | Intrahepatic cholangiocarcinoma | Peritoneal seeding | IV | 84 | 126 |
| 19 | Intrahepatic cholangiocarcinoma | Lymph nodes | III | 47 | 123 |
| 20 | Intrahepatic cholangiocarcinoma | Lymph nodes | III | 9 | 30 |
| 21 | Hilar cholangiocarcinoma | Neck lymph nodes | IV | 7 | 30 |
| 22 | Intrahepatic cholangiocarcinoma | Lymph nodes | IV | 6 | 20 |
| 23 | Intrahepatic cholangiocarcinoma | No distant metastasis | III | 5 | 20 |
| 24 | Intrahepatic cholangiocarcinoma | Distant lymph nodes | IV | 3 | 10 |
| 25 | Intrahepatic cholangiocarcinoma | Lymph node recurrence | III | 30 | 50 |
| 26 | Intrahepatic cholangiocarcinoma | Peritoneal seeding | IV | 38 | 75 |
| 27 | Intrahepatic cholangiocarcinoma | Lymph nodes | III | 38 | 121 |
| 28 | Intrahepatic cholangiocarcinoma | Liver metastasis | IV | 35 | 80 |
| 29 | Hilar cholangiocarcinoma | lymph nodes | III | 16 | 50 |
| 30 | Intrahepatic cholangiocarcinoma | No distant metastasis | III | 3 | 20 |
| 31 | cholangiocarcinoma | Lymph nodes | IV | 3 | 7 |
| 32 | Intrahepatic cholangiocarcinoma | No distant metastasis | IV | 7 | 25 |
| 33 | Intrahepatic cholangiocarcinoma | liver | IV | 13 | 25 |
| 34 | Intrahepatic cholangiocarcinoma | Peritoneal seeding | IV | 17 | 30 |
| 35 | cholangiocarcinoma | Lymph nodes | III | 1 | 5 |
| 36 | cholangiocarcinoma | Lymph nodes | IV | 30 | 50 |
| 37 | cholangiocarcinoma | Lymph nodes | III | 19 | 35 |
| 38 | cholangiocarcinoma | Lymph nodes | IV | 10 | 25 |
| 39 | Intrahepatic cholangiocarcinoma | Peritoneal seeding | IV | 4 | 7 |
| 40 | Intrahepatic cholangiocarcinoma | liver | IV | 22 | 55 |
| 41 | cholangiocarcinoma | Lymph nodes | IV | 1 | 3 |
| 42 | cholangiocarcinoma | Lymph nodes | IV | 6 | 12 |
| 43 | Intrahepatic cholangiocarcinoma | No distant metastasis | III | 2 | 5 |
| 44 | Intrahepatic cholangiocarcinoma | Lymph nodes | IV | 3 | 8 |
| 45 | Intrahepatic cholangiocarcinoma | No distant metastasis | IV | 6 | 16 |
| 46 | Intrahepatic cholangiocarcinoma | liver | IV | 2 | 6 |
| 47 | Intrahepatic cholangiocarcinoma | Peritoneal seeding | IV | 27 | 64 |
| 48 | cholangiocarcinoma | Lymph nodes | III | 11 | 24 |
| 49 | Intrahepatic cholangiocarcinoma | Lymph nodes | IV | 1 | 4 |
| 50 | cholangiocarcinoma | Lymph nodes | III | 1 | 3 |
| 51 | Intrahepatic cholangiocarcinoma | liver | IV | 55 | 98 |
| 52 | cholangiocarcinoma | Lymph nodes | IV | 72 | 128 |
| 53 | Intrahepatic cholangiocarcinoma | liver | III | 97 | 200 |
| 54 | Intrahepatic cholangiocarcinoma | Lymph nodes | IV | 12 | 36 |
| 55 | Intrahepatic cholangiocarcinoma | Lymph nodes | IV | 1 | 3 |
| 56 | Intrahepatic cholangiocarcinoma | Lymph nodes | IV | 5 | 12 |
| 57 | cholangiocarcinoma | Lymph nodes | III | 5 | 10 |

TABLE 1-continued

Number of CTCs isolated/mL of blood. Information of the disease, organ of metastasis, stage and number of CTCs isolated using MB-SCH45 or MB-anti-EpCAM

| | | | | No. of CTC isolated | |
|---|---|---|---|---|---|
| Sample # | Disease | Organ of metastasis | Stage | MB-SCH45 | MB-anti-EpCAM |
| 58 | Intrahepatic cholangiocarcinoma | liver | IV | 9 | 22 |
| 59 | Intrahepatic cholangiocarcinoma | liver | IV | 1 | 3 |
| 60 | Multiple Intrahepatic cholangiocarcinoma | No distant metastasis | IV | 4 | 9 |
| 61 | Intrahepatic cholangiocarcinoma | Lymph nodes | IV | 1 | 4 |
| 62 | Intrahepatic cholangiocarcinoma | Lymph nodes | IV | 5 | 12 |
| 63 | cholangiocarcinoma | Lymph nodes | III | 1 | 4 |
| 64 | Intrahepatic cholangiocarcinoma | liver | III | 23 | 59 |
| 65 | Multiple Intrahepatic cholangiocarcinoma | liver | IV | 15 | 37 |

Figure 2:
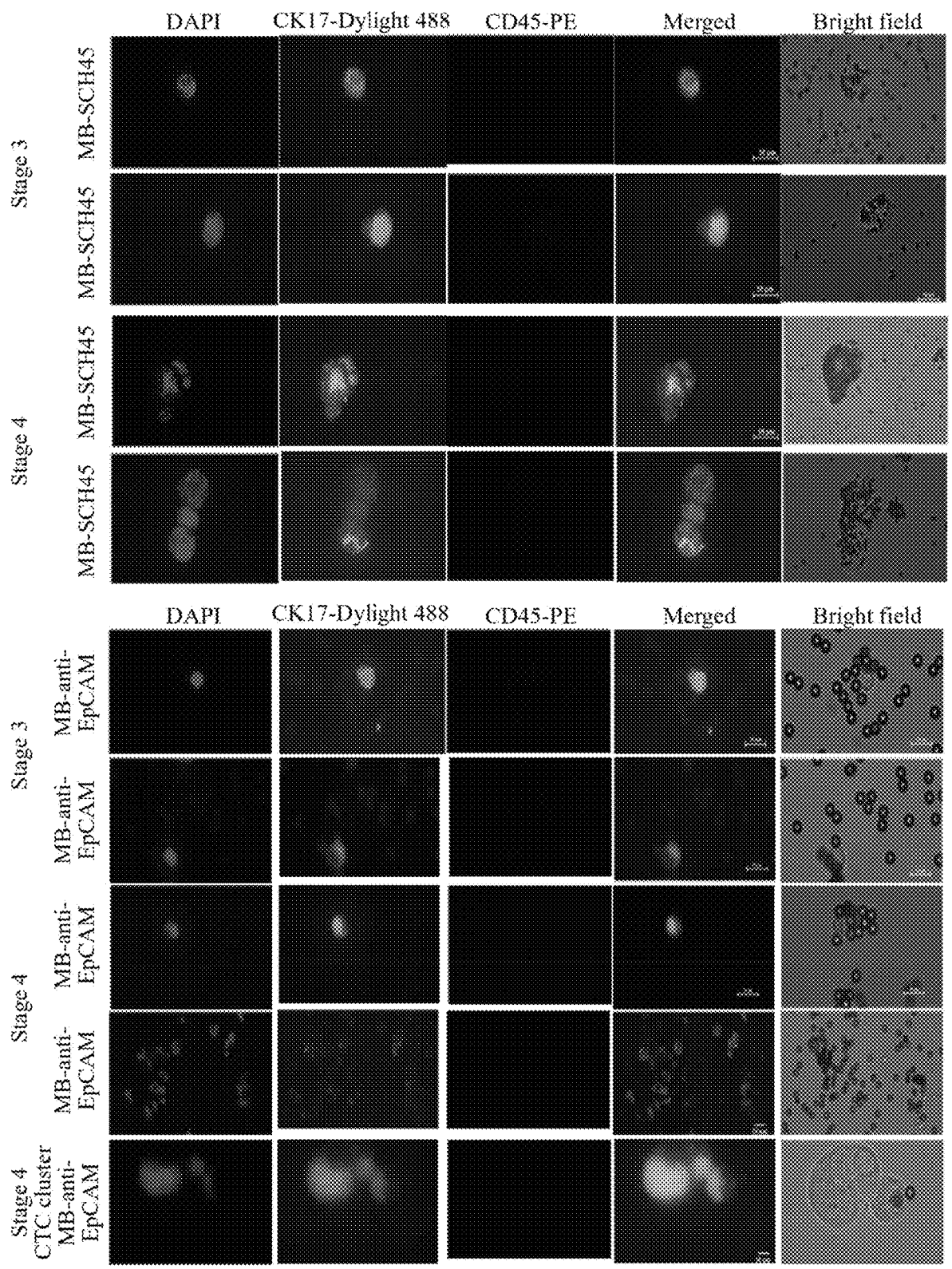
FIG. 2: Photographs depicting immunofluorescence staining of CTC clusters captured by MB-SCH45 or MB-anti-EpCAM. Negative depletion with anti-CD45 Ab and positive enrichment with MB-SCH45 (top 16 panels) and MB-anti-EpCAM (lower 20 panels) for both representative stage III and IV samples. The bottom 4 panels show the CTC culsters after positive enrichment with MB-anti-EpCAM.

The immunofluorescence images of some samples are shown in FIG. 2. It is worth mentioning that the samples were randomly selected and in no particular order. CTC clusters could be observed using both MB-SCH4 and MB-anti-EpCAM in some stage IV patients. Some clusters were relatively small while others comprised dozens of tumor cells. The CTC clusters were more evident when MB-anti-EpCAM was used for positive enrichment and have been shown in FIG. 2 (the bottom-most 4 panels). Such cluster-forming CTCs are known to have a relatively higher potential for metastasis and should be studied in detail in future works.

Example 3 CTCs in Assessing Disease Status

Figure 3:
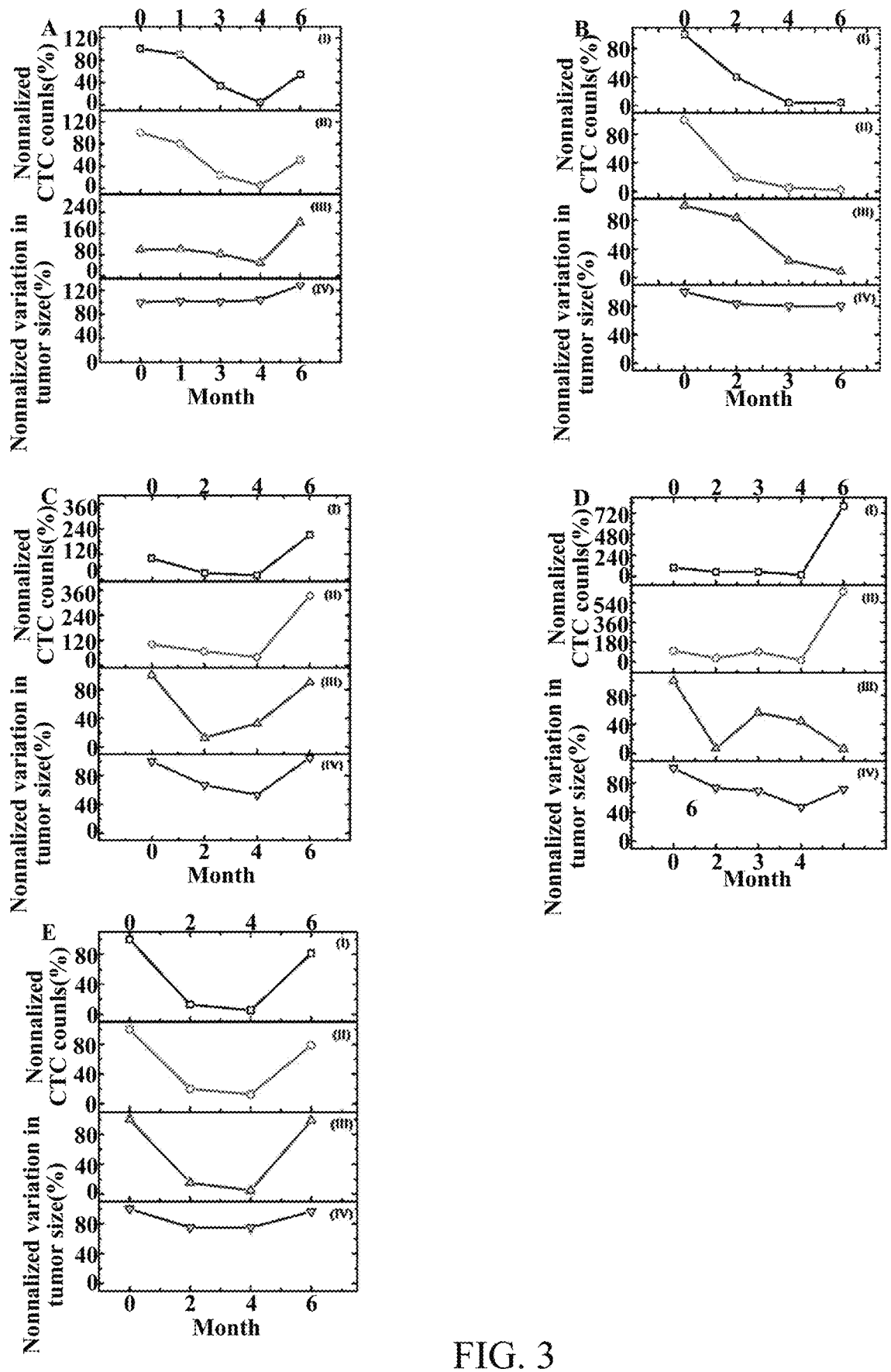
FIG. 3: The predictive significance of CTC counts. The correlation between CTC count and clinical response to chemotherapy in 5 advanced or metastatic CCA patients was tested. Panels (A) to (E) represent patients A to E. Subpanels I-III in each panel represent normalized CTC counts isolated using MB-SCH45, MB-anti-EpCAM and FACS, respectively. Subpanel IV represents the normalized tumor size using radiographic imaging.

In this example, the correlation between CTC enumeration and treatment response based on standard radiographic examination was investigated by analyzing medical records of 5 patients with advanced or metastatic CCA (i.e., patients A to E). Detailed information of these 5 patients with treatment strategy and regiments is summarized in Table 2. The number of CTCs and tumor size before treatment were treated as 100%, and the after-treatment data pertaining to individual cell number profiles and tumor size measurements were normalized to the above. The results of normalized CTC isolation using MB-SCH45, MB-anti-EpCAM, and flow assisted cell sorting (FACS) alongside computed tomography (CT) scan tumor measurements are illustrated in FIG. 3. It was found that CTCs could be successfully detected in all patients, even after several lines of chemotherapy. The total number of CTCs after the first round of treatment decreased when compared with that before treatment in all cases and corresponded with the radiographic response in all cases tested. An increased number of CTCs was observed in patients A, C and D after few lines of chemotherapy which later seemed to corroborate the radiographic finding that the tumor size had increased in these patients. These results not only implied the predictive role of CTCs for therapeutic efficacies in all patients, but also appeared to prognosticate the response to chemotherapy, often predicting the efficacy of treatment before radiographic results. The data were comparable using MB-SCH45 (patients A, B and D), or even better (patients C and E) than FACS analysis. Similar trend was also observed using MB-EpCAM. Taken together, the results demonstrated a prognostic and predictive relevance of persisting CTCs during chemotherapy, indicating a potential role of the present compound of formula (I) in monitoring of CCA treatment.

TABLE 2

Information of patients A to E.

| Patient/Age/Sex | Disease | Stage | Type of chemotherapy |
|---|---|---|---|
| Patient A/47/F | Intrahepatic cholangiocarcinoma with peritoneal seeding | IV | S-1[a], leucovorin (LV), oxaliplatin and gemcitabine (SLOG) |
| Patient B/65/M | cholangiocarcinoma with lymph node metastasis | IV | gemcitabine and cisplatin |
| Patient C/83/F | Intrahepatic cholangiocarcinoma with no distant metastasis | III | Concurrent radiotherapy followed by oral chemotherapy of S-1 |
| Patient D/46/M | Multiple Intrahepatic cholangiocarcinoma with vessel invasion | IV | S-1, leucovorin (LV), oxaliplatin and gemcitabine (SLOG) |
| Patient E/66/F | Cholangiocarcinoma with lymph node metastasis | IV | S-1, leucovorin (LV), oxaliplatin and gemcitabine (SLOG) |

[a]S-1 is a combination of tegafur, 5-chloro-2,4-dihydropyrimidine (CDHP), and potassium oxonate.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:
1. A compound of formula (I),

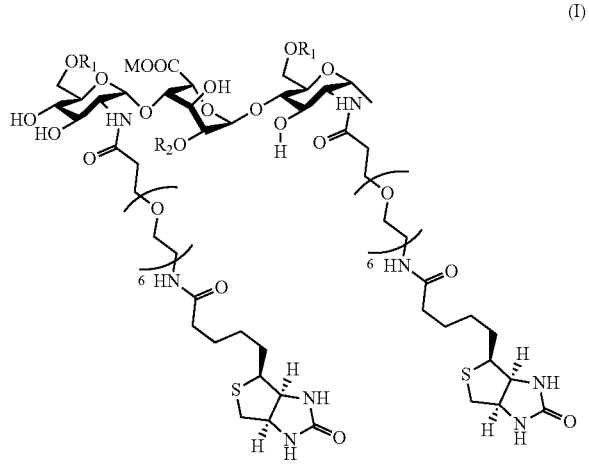

39

-continued

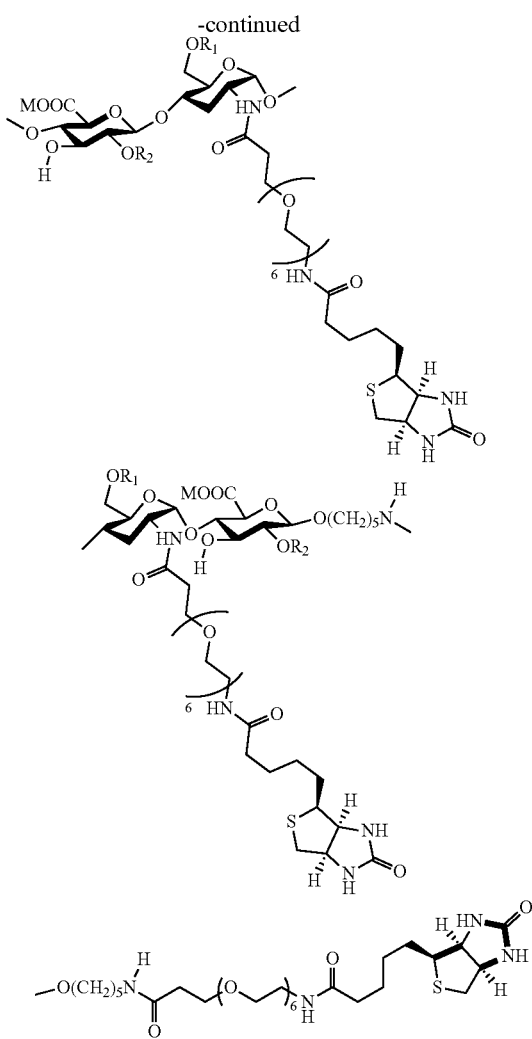

wherein, $R_1$ and $R_2$ are independently H or —$SO_3M$; and M is a monovalent cation selected from the group consisting of sodium ion, potassium ion, lithium ion or ammonium ion.

2. The compound of claim 1, wherein in the formula (I), $R_1$ and $R_2$ are independently —$SO_3M$, and M is the sodium ion.

3. A method of treating and detecting circulating cholangio-cancerous cells from a biological sample of a subject suspected of having cholangiocarcinoma (CCA) comprising:

(a) contacting the biological sample with the compound of claim 1; and (b) detecting a complex formed between the compound of claim 1 and the biological sample in an immunoassay; and (c) administering to the subject an effective amount of a chemotherapeutic agent to ameliorate symptoms associated with the CCA.

4. The method of claim 3, wherein in the formula (I), $R_1$ and $R_2$ are independently —$SO_3M$, and M is the sodium ion.

5. The method of claim 3, wherein the compound of claim 1 is coupled to streptavidin, which is pre-conjugated on the outer surface of a magnetic bead.

6. The method of claim 3, wherein the biological sample is selected from the group consisting of blood, plasma, serum, urine, sputum, saliva, tissue sample, biopsy, and tissue lysate.

7. The method of claim 6, wherein the biological sample is the blood.

8. The method of claim 7, further comprising pre-treating the blood with a lysis buffer to lyse red blood cells therein before the step (a).

9. The method of claim 3, wherein the subject has stage III or IV CCA, or metastatic CCA.

10. The method of claim 3, wherein in the step (c), the chemotherapeutic agent is selected from the group consisting of S-1, leucovorin, oxaliplatin, gemcitabine, cisplatin, and a combination thereof.

11. The method of claim 10, the S-1 is a combination of tegafur, 5-chloro-2,4-dihydropyrimidine (CDHP), and potassium oxonate.

12. The method of claim 10, wherein in the step (c), the therapeutic agent is a combination of gemcitabine and cisplatin.

* * * * *